(12) United States Patent
Lee et al.

(10) Patent No.: US 11,805,815 B2
(45) Date of Patent: Nov. 7, 2023

(54) HEATER ASSEMBLY AND AEROSOL GENERATION DEVICE COMPRISING SAME

(71) Applicant: KT&G CORPORATION, Daejeon (KR)

(72) Inventors: Jong Sub Lee, Seongnam-si (KR); Hwi Kyeong An, Seoul (KR)

(73) Assignee: KT&G CORPORATION, Daejeon (KR)

( * ) Notice: Subject to any disclaimer, the term of this patent is extended or adjusted under 35 U.S.C. 154(b) by 0 days.

(21) Appl. No.: 16/617,207

(22) PCT Filed: May 25, 2018

(86) PCT No.: PCT/KR2018/005945
§ 371 (c)(1),
(2) Date: Nov. 26, 2019

(87) PCT Pub. No.: WO2018/217054
PCT Pub. Date: Nov. 29, 2018

(65) Prior Publication Data
US 2020/0086068 A1    Mar. 19, 2020

(30) Foreign Application Priority Data

May 26, 2017 (KR) .................. 10-2017-0065550
Sep. 6, 2017 (KR) .................. 10-2017-0113954
May 24, 2018 (KR) .................. 10-2018-0059279

(51) Int. Cl.
*A24F 13/00* (2006.01)
*A24F 17/00* (2006.01)
(Continued)

(52) U.S. Cl.
CPC .......... *A24F 40/46* (2020.01); *A61M 11/042* (2014.02); *A24F 40/20* (2020.01)

(58) Field of Classification Search
CPC ....... A24F 40/46; A24F 40/20; A61M 11/042; A61M 15/06
See application file for complete search history.

(56) References Cited

U.S. PATENT DOCUMENTS 2,638,904 A    5/1953   Mitchell
4,585,014 A    4/1986   Fry
(Continued)

FOREIGN PATENT DOCUMENTS

CA    2 973 143 A1    8/2016
CA    2 975 654 A1    8/2016
(Continued)

OTHER PUBLICATIONS

Extended European Search Report dated Jan. 14, 2021 in European Application No. 18783776.0.
(Continued)

*Primary Examiner* — Abdullah A Riyami
*Assistant Examiner* — Thang H Nguyen
(74) *Attorney, Agent, or Firm* — Sughrue Mion, PLLC

(57) ABSTRACT

A heater assembly includes a heater extending to correspond to at least a part of a length of a cigarette and comprising one end to be inserted into the cigarette and configured to generate heat when electricity is applied; a first cover coupled to the heater to maintain a position with respect to the heater and comprising one surface that faces toward the end of the heater and extends outward from the heater; and a second cover coupled to another end of the heater and supporting another surface of the first cover facing toward the other end of the heater.

18 Claims, 11 Drawing Sheets

(51) Int. Cl.
*A24F 25/00* (2006.01)
*A24F 40/46* (2020.01)
*A61M 11/04* (2006.01)
*A24F 40/20* (2020.01)

(56) References Cited

U.S. PATENT DOCUMENTS

| | | | |
|---|---|---|---|
| 4,637,407 A | 1/1987 | Bonanno et al. | |
| 5,144,962 A | 9/1992 | Counts et al. | |
| 5,240,012 A | 8/1993 | Ehrman et al. | |
| 5,249,586 A | 10/1993 | Morgan et al. | |
| 5,369,723 A | 11/1994 | Counts et al. | |
| 5,388,594 A | 2/1995 | Counts et al. | |
| 5,465,738 A | 11/1995 | Rowland | |
| 5,479,948 A | 1/1996 | Counts et al. | |
| 5,499,636 A | 3/1996 | Baggett, Jr. et al. | |
| 5,591,368 A | 1/1997 | Fleischhauer et al. | |
| 5,666,977 A | 9/1997 | Higgins et al. | |
| 5,878,752 A | 3/1999 | Adams et al. | |
| 5,967,148 A | 10/1999 | Harris et al. | |
| 6,026,820 A | 2/2000 | Baggett, Jr. et al. | |
| 6,040,560 A | 3/2000 | Fleischhauer et al. | |
| 6,053,176 A * | 4/2000 | Adams | A24F 40/53 131/329 |
| 6,418,938 B1 | 7/2002 | Fleischhauer et al. | |
| 6,532,965 B1 | 3/2003 | Abhulimen et al. | |
| 6,810,883 B2 | 11/2004 | Felter et al. | |
| 7,861,726 B1 | 1/2011 | Lukasavitz | |
| 8,375,959 B2 | 2/2013 | Dittrich et al. | |
| 8,752,545 B2 | 6/2014 | Buchberger | |
| 8,851,081 B2 | 10/2014 | Fernando et al. | |
| 8,973,587 B2 | 3/2015 | Liu | |
| 9,078,472 B2 | 7/2015 | Liu | |
| 9,078,473 B2 | 7/2015 | Worm et al. | |
| 9,220,304 B2 | 12/2015 | Greim | |
| 9,271,528 B2 | 3/2016 | Liu | |
| 9,320,299 B2 | 4/2016 | Hearn et al. | |
| 9,423,152 B2 | 8/2016 | Ampolini et al. | |
| 9,427,023 B2 | 8/2016 | Liu | |
| 9,497,991 B2 | 11/2016 | Besso et al. | |
| 9,499,332 B2 | 11/2016 | Fernando et al. | |
| 9,504,279 B2 | 11/2016 | Chen | |
| 9,516,899 B2 | 12/2016 | Plojoux et al. | |
| 9,560,883 B2 | 2/2017 | Hawes | |
| 9,655,383 B2 | 5/2017 | Holzherr et al. | |
| 9,693,587 B2 | 7/2017 | Plojoux et al. | |
| 9,723,871 B2 | 8/2017 | Xiang | |
| 9,795,166 B2 | 10/2017 | Liu | |
| 9,814,263 B2 | 11/2017 | Cochand et al. | |
| 9,854,841 B2 | 1/2018 | Ampolini et al. | |
| 9,894,934 B2 | 2/2018 | Li et al. | |
| 9,918,494 B2 | 3/2018 | Mironov et al. | |
| 9,955,724 B2 | 5/2018 | Lord | |
| 9,986,760 B2 | 6/2018 | Macko et al. | |
| 9,999,247 B2 | 6/2018 | Ruscio et al. | |
| 10,015,990 B2 | 7/2018 | Mironov | |
| 10,031,183 B2 | 7/2018 | Novak, III et al. | |
| 10,070,667 B2 | 9/2018 | Lord et al. | |
| 10,104,911 B2 | 10/2018 | Thorens et al. | |
| 10,130,780 B2 | 11/2018 | Talon | |
| 10,136,673 B2 | 11/2018 | Mironov | |
| 10,194,697 B2 | 2/2019 | Fernando et al. | |
| 10,299,513 B2 | 5/2019 | Perez et al. | |
| 10,439,419 B2 | 10/2019 | Bernauer et al. | |
| 10,440,987 B2 | 10/2019 | Zeng et al. | |
| 10,448,670 B2 | 10/2019 | Talon et al. | |
| 10,492,542 B1 | 12/2019 | Worm et al. | |
| 10,548,350 B2 | 2/2020 | Greim et al. | |
| 10,555,553 B2 | 2/2020 | Binassi et al. | |
| 10,555,555 B2 | 2/2020 | Fernando et al. | |
| 10,588,351 B2 | 3/2020 | Ricketts | |
| 10,617,149 B2 | 4/2020 | Malgat et al. | |
| 10,645,971 B2 | 5/2020 | Zitzke | |
| 10,667,329 B2 | 5/2020 | Bernauer et al. | |
| 10,668,058 B2 | 6/2020 | Rose et al. | |
| 10,716,329 B2 | 7/2020 | Matsumoto et al. | |
| 10,757,975 B2 | 9/2020 | Batista et al. | |
| 10,813,174 B2 | 10/2020 | Schneider et al. | |
| 10,869,499 B2 | 12/2020 | Fernando et al. | |
| 10,869,503 B2 | 12/2020 | Yamada et al. | |
| 10,881,131 B2 | 1/2021 | Matsumoto et al. | |
| 10,881,137 B2 | 1/2021 | Suzuki et al. | |
| 10,881,143 B2 | 1/2021 | Suzuki et al. | |
| 11,039,642 B2 | 6/2021 | Zuber et al. | |
| 11,147,316 B2 | 10/2021 | Farine et al. | |
| 11,445,576 B2 | 9/2022 | Zinovik et al. | |
| 2003/0154991 A1 | 8/2003 | Fournier et al. | |
| 2004/0261802 A1 | 12/2004 | Griffin et al. | |
| 2005/0045198 A1 | 3/2005 | Larson et al. | |
| 2005/0172976 A1 | 8/2005 | Newman et al. | |
| 2006/0030214 A1 | 2/2006 | Katou et al. | |
| 2008/0001052 A1 | 1/2008 | Kalous et al. | |
| 2010/0001538 A1 | 1/2010 | Kim et al. | |
| 2010/0024834 A1 | 2/2010 | Oglesby et al. | |
| 2010/0307518 A1 | 12/2010 | Wang | |
| 2011/0155151 A1 * | 6/2011 | Newman | A24C 5/01 131/194 |
| 2011/0209717 A1 | 9/2011 | Han | |
| 2011/0226236 A1 | 9/2011 | Buchberger | |
| 2011/0265806 A1 | 11/2011 | Alarcon et al. | |
| 2011/0290248 A1 | 12/2011 | Schennum | |
| 2011/0290269 A1 * | 12/2011 | Shimizu | A24F 40/46 131/330 |
| 2012/0048266 A1 | 3/2012 | Alelov | |
| 2012/0234821 A1 * | 9/2012 | Shimizu | A24F 40/50 219/227 |
| 2012/0247494 A1 * | 10/2012 | Oglesby | A24F 42/60 131/331 |
| 2013/0014772 A1 | 1/2013 | Liu | |
| 2013/0037041 A1 | 2/2013 | Worm et al. | |
| 2013/0074857 A1 | 3/2013 | Buchberger | |
| 2013/0213419 A1 | 8/2013 | Tucker et al. | |
| 2013/0284192 A1 | 10/2013 | Peleg et al. | |
| 2013/0306064 A1 | 11/2013 | Thorens et al. | |
| 2013/0319439 A1 | 12/2013 | Gorelick et al. | |
| 2013/0319999 A1 | 12/2013 | Plojoux et al. | |
| 2013/0340775 A1 | 12/2013 | Juster et al. | |
| 2014/0014125 A1 | 1/2014 | Fernando et al. | |
| 2014/0020698 A1 | 1/2014 | Fiebelkorn | |
| 2014/0096782 A1 | 4/2014 | Ampolini et al. | |
| 2014/0116455 A1 | 5/2014 | Youn | |
| 2014/0246035 A1 | 9/2014 | Minskoff et al. | |
| 2014/0299137 A1 | 10/2014 | Kieckbusch et al. | |
| 2014/0301721 A1 | 10/2014 | Ruscio et al. | |
| 2014/0318559 A1 | 10/2014 | Thorens et al. | |
| 2014/0345634 A1 | 11/2014 | Zuber et al. | |
| 2014/0363145 A1 | 12/2014 | Plojoux et al. | |
| 2015/0007838 A1 | 1/2015 | Fernando et al. | |
| 2015/0013696 A1 * | 1/2015 | Plojoux | A61M 15/06 131/328 |
| 2015/0020832 A1 | 1/2015 | Greim et al. | |
| 2015/0024355 A1 | 1/2015 | Ghofrani et al. | |
| 2015/0027474 A1 | 1/2015 | Zuber et al. | |
| 2015/0100441 A1 | 4/2015 | Alarcon et al. | |
| 2015/0136124 A1 | 5/2015 | Aronie et al. | |
| 2015/0136154 A1 * | 5/2015 | Mitrev | A24D 1/20 131/328 |
| 2015/0181942 A1 | 7/2015 | Holzherr et al. | |
| 2015/0208725 A1 | 7/2015 | Tsai | |
| 2015/0208730 A1 | 7/2015 | Li et al. | |
| 2015/0245654 A1 | 9/2015 | Memari et al. | |
| 2015/0245666 A1 | 9/2015 | Memari et al. | |
| 2015/0257445 A1 | 9/2015 | Henry, Jr. et al. | |
| 2015/0272211 A1 | 10/2015 | Chung | |
| 2016/0137395 A1 | 5/2016 | Fernando et al. | |
| 2016/0150824 A1 | 6/2016 | Memari et al. | |
| 2016/0235121 A1 | 8/2016 | Rogan et al. | |
| 2016/0270437 A1 | 9/2016 | Nappi | |
| 2016/0286861 A1 | 10/2016 | Liu | |
| 2016/0302488 A1 | 10/2016 | Fernando et al. | |
| 2016/0331032 A1 | 11/2016 | Malgat et al. | |
| 2016/0345629 A1 | 12/2016 | Mironov | |
| 2016/0360794 A1 * | 12/2016 | Li | H05B 3/46 |
| 2016/0366946 A1 | 12/2016 | Murison et al. | |

(56) References Cited

U.S. PATENT DOCUMENTS

| | | | |
|---|---|---|---|
| 2017/0006916 A1 | 1/2017 | Liu | |
| 2017/0006919 A1 | 1/2017 | Liu | |
| 2017/0027221 A1* | 2/2017 | Liu | A24F 40/95 |
| 2017/0027229 A1 | 2/2017 | Cameron | |
| 2017/0027234 A1 | 2/2017 | Farine et al. | |
| 2017/0042243 A1 | 2/2017 | Plojoux et al. | |
| 2017/0055580 A1 | 3/2017 | Blandino et al. | |
| 2017/0071251 A1 | 3/2017 | Goch | |
| 2017/0071259 A1 | 3/2017 | Yamada et al. | |
| 2017/0095003 A1* | 4/2017 | Mironov | H05B 6/108 |
| 2017/0095006 A1 | 4/2017 | Egoyants et al. | |
| 2017/0150757 A1 | 6/2017 | Worm et al. | |
| 2017/0164659 A1 | 6/2017 | Schneider et al. | |
| 2017/0172214 A1* | 6/2017 | Li | H05B 3/26 |
| 2017/0172215 A1* | 6/2017 | Li | H05B 3/42 |
| 2017/0188634 A1 | 7/2017 | Plojoux et al. | |
| 2017/0295844 A1 | 10/2017 | Thevenaz et al. | |
| 2018/0177234 A1 | 6/2018 | Lee | |
| 2018/0206556 A1 | 7/2018 | Thorens et al. | |
| 2018/0235283 A1 | 8/2018 | Zuber et al. | |
| 2018/0289073 A1* | 10/2018 | Guo | A24F 40/46 |
| 2019/0075849 A1 | 3/2019 | Hawes | |
| 2019/0252888 A1 | 8/2019 | Holzherr | |
| 2019/0320719 A1 | 10/2019 | Liu et al. | |
| 2019/0364975 A1 | 12/2019 | Fernando et al. | |
| 2020/0006950 A1 | 1/2020 | Holzherr | |
| 2020/0046028 A1* | 2/2020 | Oh | H05B 3/46 |
| 2020/0120983 A1 | 4/2020 | Chen | |
| 2020/0154768 A1* | 5/2020 | Han | A24F 40/60 |
| 2020/0232766 A1 | 7/2020 | Flick | |
| 2020/0305508 A1 | 10/2020 | Talon | |
| 2020/0352224 A1* | 11/2020 | Plojoux | H05B 1/0244 |
| 2020/0359681 A1* | 11/2020 | Han | A24F 40/95 |
| 2020/0359682 A1* | 11/2020 | Han | A24F 40/95 |
| 2020/0413495 A1 | 12/2020 | Schneider et al. | |
| 2021/0000182 A1 | 1/2021 | Ruscio et al. | |
| 2021/0120875 A1 | 4/2021 | Mironov | |

FOREIGN PATENT DOCUMENTS

| | | | |
|---|---|---|---|
| CH | 310239 A | 12/1955 | |
| CN | 2146758 Y | 11/1993 | |
| CN | 1102964 A | 5/1995 | |
| CN | 1122213 A | 5/1996 | |
| CN | 1190335 A | 8/1998 | |
| CN | 1209731 A | 3/1999 | |
| CN | 2857109 Y | 1/2007 | |
| CN | 1973706 A | 6/2007 | |
| CN | 101043827 A | 9/2007 | |
| CN | 101444335 A | 6/2009 | |
| CN | 201491717 U | 6/2010 | |
| CN | 101940369 A | 1/2011 | |
| CN | 102006790 A | 4/2011 | |
| CN | 102109393 A | 6/2011 | |
| CN | 10232689 A | 1/2012 | |
| CN | 102438470 A | 5/2012 | |
| CN | 202407082 U | 9/2012 | |
| CN | 202774134 U | 3/2013 | |
| CN | 103096741 A | 5/2013 | |
| CN | 103281920 A | 9/2013 | |
| CN | 103338665 A | 10/2013 | |
| CN | 103622162 A | 3/2014 | |
| CN | 203457802 U | 3/2014 | |
| CN | 203575658 U | 5/2014 | |
| CN | 103859606 A | 6/2014 | |
| CN | 203633505 U | 6/2014 | |
| CN | 203646503 U | 6/2014 | |
| CN | 103929988 A | 7/2014 | |
| CN | 203689071 U | 7/2014 | |
| CN | 203692545 U | 7/2014 | |
| CN | 103974638 A | 8/2014 | |
| CN | 103974640 A | 8/2014 | |
| CN | 103987286 A | 8/2014 | |
| CN | 103997921 A | 8/2014 | |
| CN | 103997922 A | 8/2014 | |
| CN | 203789137 U | 8/2014 | |
| CN | 104023568 A | 9/2014 | |
| CN | 104023574 A | 9/2014 | |
| CN | 104039183 A | 9/2014 | |
| CN | 203814592 U | 9/2014 | |
| CN | 104095295 A | 10/2014 | |
| CN | 104106842 A | 10/2014 | |
| CN | 203943078 U | 11/2014 | |
| CN | 204070570 U | 1/2015 | |
| CN | 204146338 U | 2/2015 | |
| CN | 102811634 B | 3/2015 | |
| CN | 104382237 A | 3/2015 | |
| CN | 104470387 A | 3/2015 | |
| CN | 104489933 A | 4/2015 | |
| CN | 104544559 A | 4/2015 | |
| CN | 204317504 U | 5/2015 | |
| CN | 204393344 U | 6/2015 | |
| CN | 104754964 A | 7/2015 | |
| CN | 104770878 A | 7/2015 | |
| CN | 104799438 A | 7/2015 | |
| CN | 104812260 A | 7/2015 | |
| CN | 204444239 U | 7/2015 | |
| CN | 204763414 U | 11/2015 | |
| CN | 105163610 A | 12/2015 | |
| CN | 105208882 A | 12/2015 | |
| CN | 105208884 A | 12/2015 | |
| CN | 105341993 A | 2/2016 | |
| CN | 105342011 A | 2/2016 | |
| CN | 105357994 A | 2/2016 | |
| CN | 205018293 U | 2/2016 | |
| CN | 105361250 A | 3/2016 | |
| CN | 105453598 A | 3/2016 | |
| CN | 205072064 U | 3/2016 | |
| CN | 205180371 U | 4/2016 | |
| CN | 205197003 U | 5/2016 | |
| CN | 205337598 U | 6/2016 | |
| CN | 105747281 A | 7/2016 | |
| CN | 105789506 A | 7/2016 | |
| CN | 105831812 A | 8/2016 | |
| CN | 105848503 A | 8/2016 | |
| CN | 105876869 A | 8/2016 | |
| CN | 205456048 U | 8/2016 | |
| CN | 205512358 U | 8/2016 | |
| CN | 105939625 A | 9/2016 | |
| CN | 205597118 U | 9/2016 | |
| CN | 106037014 A | 10/2016 | |
| CN | 205648910 U | 10/2016 | |
| CN | 106102492 A | 11/2016 | |
| CN | 106132217 A | 11/2016 | |
| CN | 106163307 A | 11/2016 | |
| CN | 205728067 U | 11/2016 | |
| CN | 106174699 A | 12/2016 | |
| CN | 106231934 A | 12/2016 | |
| CN | 205831062 U | 12/2016 | |
| CN | 106413439 A | 2/2017 | |
| CN | 106413444 A | 2/2017 | |
| CN | 106455708 A | 2/2017 | |
| CN | 106455714 A | 2/2017 | |
| CN | 106455716 A | 2/2017 | |
| CN | 106473233 A | 3/2017 | |
| CN | 106535680 A | 3/2017 | |
| CN | 206097720 U | 4/2017 | |
| CN | 206197012 U | 5/2017 | |
| CN | 106901404 A | 6/2017 | |
| CN | 206312988 U | 7/2017 | |
| CN | 107770883 A | 3/2018 | |
| DE | 3302518 A1 | 7/1984 | |
| DE | 20 2014 004 361 U1 | 9/2001 | |
| EA | 012169 B1 | 8/2009 | |
| EA | 026076 B1 | 2/2017 | |
| EP | 1119267 B1 | 7/2004 | |
| EP | 2 110 033 A1 | 10/2009 | |
| EP | 2 201 850 A1 | 6/2010 | |
| EP | 2253233 A1 | 11/2010 | |
| EP | 2 022 349 B1 | 7/2014 | |
| EP | 2 531 053 B1 | 9/2015 | |
| EP | 3 098 738 A1 | 11/2016 | |
| EP | 2 432 339 B1 | 3/2017 | |
| EP | 3 179 828 A1 | 6/2017 | |

(56) References Cited

FOREIGN PATENT DOCUMENTS

| | | |
|---|---|---|
| EP | 3 248 485 B1 | 4/2020 |
| EP | 3 275 319 B1 | 8/2020 |
| GB | 2542018 A | 3/2017 |
| GB | 2550540 A | 11/2017 |
| JP | 3-232481 A | 10/1991 |
| JP | 7-184627 A | 7/1995 |
| JP | 11-40122 A | 2/1999 |
| JP | 11-164679 A | 6/1999 |
| JP | 3645921 B2 | 5/2005 |
| JP | 2006-092831 A | 4/2006 |
| JP | 2006-320286 A | 11/2006 |
| JP | 4278306 B2 | 6/2009 |
| JP | 2010-178730 A | 8/2010 |
| JP | 2010-526553 A | 8/2010 |
| JP | 2011-87569 A | 5/2011 |
| JP | 2011-518567 A | 6/2011 |
| JP | 4739433 B2 | 8/2011 |
| JP | 2012-527222 A | 11/2012 |
| JP | 2014-500017 A | 1/2014 |
| JP | 2014079229 A | 5/2014 |
| JP | 2014-521419 A | 8/2014 |
| JP | 2014-525237 A | 9/2014 |
| JP | 2014216287 A | 11/2014 |
| JP | 2014-533513 A | 12/2014 |
| JP | 2014-534813 A | 12/2014 |
| JP | 2015-503916 A | 2/2015 |
| JP | 2015-504669 A | 2/2015 |
| JP | 2015-506170 A | 3/2015 |
| JP | 2015-507477 A | 3/2015 |
| JP | 2015-508996 A | 3/2015 |
| JP | 2015-524261 A | 8/2015 |
| JP | 2015-180214 A | 10/2015 |
| JP | 2015-529458 A | 10/2015 |
| JP | 2015-204833 A | 11/2015 |
| JP | 2016-528910 A | 9/2016 |
| JP | 2016-538848 A | 12/2016 |
| JP | 2017-501682 A | 1/2017 |
| JP | 2017-46700 A | 3/2017 |
| JP | 2017-51189 A | 3/2017 |
| JP | 2017-70297 A | 4/2017 |
| JP | 2017-514463 A | 6/2017 |
| KR | 10-1999-0081973 A | 11/1999 |
| KR | 20-0203233 Y1 | 11/2000 |
| KR | 10-0304044 B1 | 11/2001 |
| KR | 10-0806461 B1 | 2/2008 |
| KR | 20-2009-0008911 U | 9/2009 |
| KR | 10-0965099 B1 | 6/2010 |
| KR | 10-1001077 B1 | 12/2010 |
| KR | 10-2011-0096548 A | 8/2011 |
| KR | 20-2011-0009632 U | 10/2011 |
| KR | 10-1098112 B1 | 12/2011 |
| KR | 10-2012-0027029 A | 3/2012 |
| KR | 10-2012-0101637 A | 9/2012 |
| KR | 10-1184499 B1 | 9/2012 |
| KR | 10-2012-0109634 A | 10/2012 |
| KR | 10-2012-0114333 A | 10/2012 |
| KR | 10-2012-0121314 A | 11/2012 |
| KR | 10-2013-0027909 A | 3/2013 |
| KR | 10-2013-0031025 A | 3/2013 |
| KR | 20-0466757 Y1 | 5/2013 |
| KR | 10-2013-0081238 A | 7/2013 |
| KR | 20-0465913 Y1 | 10/2013 |
| KR | 10-2013-0139296 A | 12/2013 |
| KR | 10-2014-0068203 A | 6/2014 |
| KR | 10-2014-0092312 A | 7/2014 |
| KR | 10-2014-0114554 A | 9/2014 |
| KR | 10-2014-0116055 A | 10/2014 |
| KR | 10-2014-0118983 A | 10/2014 |
| KR | 10-2014-0119072 A | 10/2014 |
| KR | 10-2014-0135774 A | 11/2014 |
| KR | 20-2014-0006242 | 12/2014 |
| KR | 10-2015-0030409 A | 3/2015 |
| KR | 10-2015-0033617 A | 4/2015 |
| KR | 10-2015-0058569 A | 5/2015 |
| KR | 10-1516304 B1 | 5/2015 |
| KR | 10-1523088 B1 | 5/2015 |
| KR | 10-1523088 B2 | 5/2015 |
| KR | 10-2015-0099771 A | 9/2015 |
| KR | 10-2016-0009678 A | 1/2016 |
| KR | 10-2016-0012110 A | 2/2016 |
| KR | 10-2016-0012329 A | 2/2016 |
| KR | 10-2016-0015144 A | 2/2016 |
| KR | 10-2016-0040643 A | 4/2016 |
| KR | 10-1609715 B1 | 4/2016 |
| KR | 10-2015-0058569 A | 5/2016 |
| KR | 10-2016-0052607 A | 5/2016 |
| KR | 10-1619032 B1 | 5/2016 |
| KR | 20-2016-0001476 U | 5/2016 |
| KR | 10-2016-0060006 A | 6/2016 |
| KR | 10-2016-0088163 A | 7/2016 |
| KR | 10-2016-0094938 A | 8/2016 |
| KR | 10-2016-0096744 A | 8/2016 |
| KR | 10-2016-0108855 A | 9/2016 |
| KR | 10-1656061 B1 | 9/2016 |
| KR | 10-2016-0114743 A | 10/2016 |
| KR | 10-2016-0124091 A | 10/2016 |
| KR | 10-1667124 B1 | 10/2016 |
| KR | 10-1668175 B1 | 10/2016 |
| KR | 10-2016-0129024 A | 11/2016 |
| KR | 10-2016-0131035 A | 11/2016 |
| KR | 10-2016-0133665 A | 11/2016 |
| KR | 10-2016-0137627 A | 11/2016 |
| KR | 10-1679489 B1 | 11/2016 |
| KR | 10-2016-0140608 A | 12/2016 |
| KR | 10-2016-0142896 A | 12/2016 |
| KR | 10-2016-0147253 A | 12/2016 |
| KR | 10-1690389 B1 | 12/2016 |
| KR | 10-2017-0006282 A | 1/2017 |
| KR | 10-2017-0007262 B2 | 1/2017 |
| KR | 10-2017-0044158 A | 4/2017 |
| KR | 10-1740160 B1 | 5/2017 |
| KR | 10-2017-0071486 A | 6/2017 |
| KR | 10-2017-0074898 A | 6/2017 |
| KR | 1020170106916 A | 9/2017 |
| RU | 2302806 C2 | 7/2007 |
| RU | 2425608 C2 | 8/2011 |
| RU | 2531890 C2 | 10/2014 |
| RU | 2564600 C1 | 10/2015 |
| RU | 2014 125 232 A | 12/2015 |
| RU | 2014125232 A | 12/2015 |
| RU | 2581999 C2 | 4/2016 |
| RU | 2589437 C2 | 7/2016 |
| RU | 2594557 C2 | 8/2016 |
| RU | 2595593 C2 | 8/2016 |
| RU | 2 602 962 C2 | 11/2016 |
| RU | 2 603 559 C2 | 11/2016 |
| RU | 2602053 C2 | 11/2016 |
| RU | 2602962 C2 | 11/2016 |
| RU | 2604012 C2 | 12/2016 |
| UA | 104628 C2 | 2/2014 |
| UA | 112169 C2 | 8/2016 |
| WO | 94/06314 A1 | 3/1994 |
| WO | 98/23171 A1 | 6/1998 |
| WO | 00/27232 A1 | 5/2000 |
| WO | 2010/133342 A1 | 11/2010 |
| WO | 2011/028372 A1 | 3/2011 |
| WO | 2011/095781 A1 | 8/2011 |
| WO | 2012/072264 A1 | 6/2012 |
| WO | 2012/123702 A1 | 9/2012 |
| WO | 2013/034458 A1 | 3/2013 |
| WO | 2013/060743 A2 | 5/2013 |
| WO | 2013/076098 A2 | 5/2013 |
| WO | 2013/093695 A1 | 6/2013 |
| WO | 2013/098395 A1 | 7/2013 |
| WO | 2013/098398 A3 | 7/2013 |
| WO | 2013/098409 A1 | 7/2013 |
| WO | 2013/102609 A2 | 7/2013 |
| WO | 2013/102612 A2 | 7/2013 |
| WO | 2013/120565 A3 | 8/2013 |
| WO | 2013/126777 A2 | 8/2013 |
| WO | 2013/137084 A1 | 9/2013 |
| WO | 2013/171217 A1 | 11/2013 |
| WO | 2014/029880 A2 | 2/2014 |
| WO | 2014/102092 A | 7/2014 |

(56) References Cited

FOREIGN PATENT DOCUMENTS

| WO | 2015/046386 A1 | 4/2015 |
|---|---|---|
| WO | 2015/088744 A1 | 6/2015 |
| WO | 2015088744 A1 | 6/2015 |
| WO | 2015/128665 A1 | 9/2015 |
| WO | 2015128665 A1 | 9/2015 |
| WO | 2015/155289 A1 | 10/2015 |
| WO | 2015/165813 A1 | 11/2015 |
| WO | 2015/174657 A1 | 11/2015 |
| WO | 2015/177044 A1 | 11/2015 |
| WO | 2015/197627 A1 | 12/2015 |
| WO | 2016/059073 A1 | 4/2016 |
| WO | 2016/075028 A1 | 5/2016 |
| WO | 2016/076147 A1 | 5/2016 |
| WO | 2016075028 A1 | 5/2016 |
| WO | 2016/107766 A1 | 7/2016 |
| WO | 2016/124550 A1 | 8/2016 |
| WO | 2016/124552 A1 | 8/2016 |
| WO | 2016/150019 A1 | 9/2016 |
| WO | 2016/156103 A1 | 10/2016 |
| WO | 2016/156219 A1 | 10/2016 |
| WO | 2016/159013 A1 | 10/2016 |
| WO | 2016166064 A1 | 10/2016 |
| WO | 2016178377 A1 | 11/2016 |
| WO | 2016187803 A1 | 12/2016 |
| WO | 2017/029088 A1 | 2/2017 |
| WO | 2017/029089 A1 | 2/2017 |
| WO | 2017029089 A1 | 2/2017 |
| WO | 2017/037457 A1 | 3/2017 |
| WO | 2017/042297 A1 | 3/2017 |
| WO | 2017/075759 A1 | 5/2017 |
| WO | 2017/139963 A1 | 8/2017 |
| WO | 2018050449 A1 | 3/2018 |
| WO | 2018/189195 A1 | 10/2018 |
| WO | 2018227593 A1 | 12/2018 |
| WO | 2019/020826 A1 | 1/2019 |
| WO | 2019/030172 A1 | 2/2019 |
| WO | 2019/095268 A1 | 5/2019 |

OTHER PUBLICATIONS

Extended European Search Report dated Jan. 25, 2021 in European Application No. 18785166.2.
Extended European Search Report dated Jan. 29, 2021 in European Application No. 18784464.2.
Extended European Search Report dated Mar. 15, 2021 in European Application No. 18785061.5.
Extended European Search Report dated Mar. 19, 2021 in European Application No. 18784164.8.
Extended European Search Report dated Mar. 24, 2021 in European Application No. 18784268.7.
Extended European Search Report dated Mar. 25, 2021 in European Application No. 18784370.1.
Extended European Search Report dated Mar. 25, 2021 in European Application No. 18784841.1.
Office Action dated Feb. 24, 2021 in Japanese Application No. 2019-555168.
Office Action dated Feb. 24, 2021 in Japanese Application No. 2019-555203.
Office Action dated Feb. 24, 2021 in Japanese Application No. 2019-555204.
Office Action dated Feb. 4, 2021 in Russian Application No. 2020124609.
Office Action dated Feb. 9, 2021 in Japanese Application No. 2019-555184.
Office Action dated Jan. 26, 2021 in Japanese Application No. 2020-501521.
Office Action dated Mar. 2, 2021 in Japanese Application No. 2019-555170.
Office Action dated Mar. 2, 2021 in Japanese Application No. 2019-555182.
Office Action dated Mar. 30, 2021 in Japanese Application No. 2020-501377.
Office Action dated Jan. 19, 2021 in Indonesian Application No. P00201906007.
International Search Report dated Dec. 4, 2018 in International Application No. PCT/KR2018/006747.
International Search Report dated Nov. 30, 2018 in International Application No. PCT/KR2018/006702.
International Search Report dated Aug. 29, 2018 in International Application No. PCT/KR2018/005945.
International Search Report dated Aug. 28, 2018 in International Application No. PCT/KR2018/005693.
International Search Report dated May 29, 2018 in International Application No. PCT/KR2017/012486.
Office Action dated Mar. 8, 2019 in Korean Application No. 10-2017-0065550.
Office Action dated Jun. 19, 2019 in Korean Application No. 10-2018-0059279.
Office Action dated Jun. 27, 2019 in Korean Application No. 10-2018-0063759.
Office Action dated Aug. 7, 2019 in Korean Application No. 10-2018-0067035.
Communication dated Jun. 11, 2020 by the Korean Patent Office in application No. 10-2018-0051469.
Office Action dated Nov. 26, 2020 from the Russian Federal Service for Intellectual Property in Application No. 2020124609/03.
Decision on Grant of a Patent For Invention dated Oct. 26, 2020 from Russian Federal Service for Intellectual Property in Application No. 2020124610/03.
Communication dated Jun. 29, 2020 from the Korean Intellectual Property Office in application No. 10-2018-0010836.
Communication dated Oct. 29, 2020 from the Korean Intellectual Property Office in application No. 10-2018-0010837.
Office Action dated Nov. 4, 2020 from the Japanese Patent Office in Application No. 2019-554453.
Office Action dated Nov. 4, 2020 from the Japanese Patent Office in Application No. 2020-128346.
Decision on Grant of a Patent For Invention dated Nov. 26, 2020 from Russian Federal Service for Intellectual Property in Application No. 2020124607/03.
Partial Supplementary European Search Report dated Aug. 3, 2020 from the European Patent Office in EP Application No. 17880867.1.
Extended European Search Report dated Nov. 4, 2020 from the European Patent Office in EP Application No. 17880867.1.
Extended European Search Report dated Dec. 11, 2020 in European Application No. 20188967.2.
Extended European Search Report dated Dec. 16, 2020 in European Application No. 20188985.4.
Office Action dated Dec. 30, 2020 in Russian Application No. 2020124651.
Office Action dated Dec. 28, 2020 in Russian Application No. 2020124652.
Office Action dated Dec. 11, 2020 in Russian Application No. 2020124653.
Office Action dated Jan. 22, 2021 in Russian Application No. 2020124657.
Office Action dated Jan. 22, 2021 in Russian Application No. 2020124658.
Extended European Search Report dated Dec. 18, 2020 in European Application No. 18775504.6.
Office Action dated Jan. 19, 2021 in Japanese Application No. 2019-553569.
Extended European Search Report dated Jan. 14, 2021 in European Application No. 18784738.9.
Extended European Search Report dated Dec. 10, 2020 in European Application No. 20188932.6.
Office Action dated Jan. 12, 2021 in Japanese Application No. 2019-555201.
Office Action dated Jan. 12, 2021 in Japanese Application No. 2019-555169.
Office Action dated Jan. 5, 2021 in Japanese Application No. 2019-558557.

(56) References Cited

OTHER PUBLICATIONS

Extended European Search Report dated Nov. 19, 2020 in European Application No. 20188792.4.
Office Action dated Dec. 1, 2020 in Japanese Application No. 2020-501188.
Extended European Search Report dated Dec. 18, 2020 in European Application No. 20188926.8.
Office Action dated Jan. 19, 2021 in Japanese Application No. 2020-501514.
Office Action dated Sep. 24, 2020 in Korean Application No. 10-2018-0012456.
Office Action dated May 28, 2020 in Korean Application No. 10-2017-0147605.
Communication dated Dec. 9, 2019, from the Korean Intellectual Property Office in application No. 10-2018-0051469.
Extended European Search Report dated Oct. 27, 2021 in European Application No. 18844735.3.
Office Action dated Oct. 28, 2021 in Chinese Application No. 201880046418.2.
Office Action dated Sep. 24, 2021 in Chinese Application No. 201880024010.5.
Office Action dated Sep. 29, 2021 in Chinese Application No. 201880024276.X.
Office Action dated Sep. 29, 2021 in Chinese Application No. 201880024311.8.
Office Action dated Nov. 25, 2021 in Chinese Application No. 201880047174.X.
Office Action dated Dec. 1, 2021 in Chinese Application No. 201880046367.3.
Communication dated Aug. 16, 2021 by the Chinese Patent Office in Chinese Application No. 201880024006.9.
Communication dated Aug. 26, 2021 by the Chinese Patent Office in Chinese Application No. 201880024107.6.
Communication dated Aug. 4, 2021 by the Chinese Patent Office in Chinese Application No. 201880024289.7.
Communication dated Jul. 16, 2021 by the Chinese Patent Office in Chinese Application No. 201880024367.3.
Communication dated Jul. 19, 2021 by the Chinese Patent Office in Chinese Application No. 201880024070.7.
Communication dated Jul. 26, 2021 by the Chinese Patent Office in Chinese Application No. 201880024059.0.
Communication dated Jul. 27, 2021 by the Chinese Patent Office in Chinese Application No. 201780084891.5.
Communication dated Sep. 17, 2021 by the Chinese Patent Office in Chinese Application No. 201880030699.2.
Office Action dated Apr. 2, 2019 in Korean Application No. 10-2019-0021286.
Office Action dated Apr. 25, 2019 in Korean Application No. 10-2019-0033721.
Office Action dated Apr. 25, 2019 in Korean Application No. 10-2019-0033784.
Office Action dated Apr. 3, 2019 in Korean Application No. 10-2019-0018812.
Office Action dated Apr. 4, 2019 in Korean Application No. 10-2019-0019194.
Office Action dated Apr. 4, 2019 in Korean Application No. 10-2019-0019195.
Office Action dated Apr. 4, 2019 in Korean Application No. 10-2019-0020484.
Office Action dated Apr. 9, 2021 in Korean Application No. 10-2020-0116256.
Extended European Search Report dated Apr. 1, 2021 in European Application No. 18805933.1.
Extended European Search Report dated Jan. 15, 2021 in European Application No. 20188949.0.
Extended European Search Report dated Jul. 1, 2021 in European Application No. 18854661.8.
Extended European Search Report dated Jun. 14, 2021 in European Application No. 18842951.8.
Extended European Search Report dated Jun. 16, 2021 in European Application No. 18853434.1.
Office Action dated Jul. 22, 2021 in Korean Application No. 10-2021-0051359.
Office Action dated Jun. 29, 2021 in Chinese Application No. 201880022072.2.
Office Action dated May 5, 2021 in Canadian Application No. 3,047,236.
International Search Report dated Feb. 28, 2019 from the International Searching Authority in International Application No. PCT/KR2018/009100.
International Search Report dated Nov. 26, 2018 from the International Searching Authority in International Application No. PCT/KR2018/009094.
International Search Report dated Jul. 24, 2018 in International Application No. PCT/KR2018/003691.
International Search Report dated Nov. 14, 2018 in International Application No. PCT/KR2018/004118.
International Search Report dated Nov. 6, 2018 in International Application No. PCT/KR2018/004129.
International Search Report dated Nov. 6, 2018 in International Application No. PCT/KR2018/004130.
International Search Report dated Nov. 6, 2018 in International Application No. PCT/KR2018/004178.
International Search Report dated Sep. 6, 2018 in International Application No. PCT/KR2018/004176.
International Search Report dated Sep. 6, 2018 in International Application No. PCT/KR2018/004179.
International Search Report dated Sep. 7, 2018 in International Application No. PCT/KR2018/004171.
International Search Report dated Sep. 7, 2018 in International Application No. PCT/KR2018/004172.
Office Action dated Apr. 5, 2019 in Korean Application No. 10-2019-0027638.
Office Action dated May 27, 2020 in Russian Application No. 2019121813.
Office Action dated Feb. 28, 2022 in Chinese Application No. 201880050526.7.
Office Action dated Mar. 14, 2022 in Chinese Application No. 201880024059.0.
Office Action issued in the Canadian Patent Office dated May 30, 2022 in corresponding Canadian Application No. 3,080,145.
Substantive Examination Report issued in the Intellectual Property Office of the Phillipines Bureau of Patents dated Jun. 9, 2022, in corresponding PH Patent Application No. 1-2019-501361.
Notice of Reasons for Refusal issued in the Japanese Patent Office dated Jun. 28, 2022, in corresponding Japanese Patent Application No. 2021-075028.
Third Office Action issued in the China National Intellectual Property Adminstration dated Aug. 12, 2022 in corresponding Chinese Patent Application No. 201880024059.0.
Notice of Reason for Refusal issued in the Japanese Patent Office dated Sep. 20, 2022 in corresponding Japanese Patent Application No. 2021-174035.
Office Action dated Nov. 22, 2022 in Chinese Application No. 202010762996.5.
Office Action dated Oct. 24, 2022 in Ukranian Application No. a 2020 014868.
Office Action dated Oct. 27, 2022 in Ukranian Application No. a 2020 04869.
Office Action dated Nov. 2, 2022 in Chinese Application No. 201880050526.7.
Notice for Reasons for Refusal issued in the Japanese Patent Office dated Dec. 13, 2022 in corresponding Japanese Patent Application No. 2021-165298.
First Office Action issued in the China National Intellectual Property Adminstration dated Dec. 30, 2022 in corresponding Chinese Patent Application No. 202010756239.7.
Notice of Reasons for Refusal dated Jan. 10, 2023 in the Japanese Patent Office in corresponding Japanese Patent Application No. 2021-177649.

(56) References Cited

OTHER PUBLICATIONS

First Office Action dated Jan. 3, 2023 in the China National Intellectual Property Adminstration in corresponding Chinese Patent Application No. 202010760978.8.
First Office Action issued in the China National Intellectual Property Adminstration dated Jan. 10, 2023 in corresponding Chinese Patent Application No. 202010760990.4.
First Office Action issued in the China National Intellectual Property Administration dated Jan. 28, 2023 in corresponding Chinese Patent Application No. 202010763214.X.
Notice of Reasons for Refusal Issued in the Japanese Patent Office dated May 9, 2023 in corresponding Japanese Patent Application No. 2022-086448.
Communication pursuant to Article 94(3) EPC issued in the European Patent Office in corresponding EP Patent Application No. 18785166.2 dated Jul. 10, 2023.
Preliminary conclusion of the qualification examination issued in the Ukrainian National Office of Intellectual Property and Innovations in corresponding UA Patent Application No. a202104884 dated Jul. 12, 2023.
Request for the Submission of an Opinion issued in the Korean Patent Office in corresponding KR Patent Application No. 10-2022-0148790 dated Jun. 1, 2023.
Third Office Action dated Jul. 31, 2023 in the China Natiional Intellectual Property Administration in corresponding Chinese Patent Application No. 201880050526.7.

\* cited by examiner

HEATER ASSEMBLY AND AEROSOL GENERATION DEVICE COMPRISING SAME

CROSS REFERENCE TO RELATED APPLICATIONS

This application is a National Stage of International Application No. PCT/KR2018/005945 filed May 25, 2018, claiming priority based on Korean Patent Application Nos. 10-2017-0065550 filed May 26, 2017, 10-2017-0113954 filed Sep. 6, 2017 and 10-2018-0059279 filed May 24, 2018.

TECHNICAL FIELD

The present disclosure relates to a heater assembly and an aerosol generation device including the same, and more particularly, to a heater assembly with enhanced durability achieved by maintaining a firm assembling state, and an aerosol generation device including the same.

BACKGROUND ART

Recently, there is a growing demand for alternative methods for resolving problems of a common cigarette. For example, there is a growing demand for a method of generating aerosol by heating an aerosol generating material in a cigarette instead of burning the cigarette to generate aerosol. Therefore, research into heating-type cigarettes or heating-type aerosol generation devices is being actively carried out.

An aerosol generation device that heats a cigarette to generate aerosol uses a heater assembly that generates heat by electricity. In the heater assembly that heats a cigarette in a state of being inserted into the cigarette, a heater may be shaken due to a loosened coupling state of components in a process of repeatedly performing an operation of inserting and separating the heater assembly into and from the cigarette. In addition, due to manufacturing tolerances of components coupled to the heater so as to support the heater, a position of the heater disposed inside of the aerosol generation device may not be stably maintained, and the heater and the components may be shaken when the cigarette is mounted or when the cigarette is separated. As such, when the assembling state of the heater assembly is defective, external impurities may be introduced into the aerosol generation device through the heater assembly, which may degrade the performance of an electronic component.

DESCRIPTION OF EXEMPLARY EMBODIMENTS

Technical Problem

Exemplary embodiments provide a heater assembly with enhanced durability and sealing performance obtained by a firm assembling state and an aerosol generation device including the same.

Exemplary embodiments also provide a heater assembly in which components for supporting a heater are firmly coupled to each other such that an occurrence of shaking of the heater is minimized and an aerosol generation device including the same.

Solution to Problem

According to an aspect of the present disclosure, a heater extending to correspond to at least a part of a length of a cigarette and comprising one end to be inserted into the cigarette and configured to generate heat when electricity is applied; a first cover coupled to the heater to maintain a position with respect to the heater and comprising one surface that faces toward the end of the heater and extends outward from the heater; and a second cover coupled to another end of the heater and supporting another surface of the first cover facing toward the other end of the heater.

The first cover may include a flange fixed to an outer surface of the heater and protruding outward from the outer surface of the heater; and an outer cover disposed closer to the one end of the heater than the flange to form the one surface, and configured to contact and support at least a part of an outer surface of the flange, and wherein the other surface of the first cover supported by the second cover is formed by the flange.

The outer cover may further include an inner protrusion protruding from an inner side of the outer cover and contacting the outer surface of the flange.

The second cover may include a mounting hole into which the other end of the heater is inserted; and a contact protrusion protruding from outside of the mounting hole toward the flange to contact the other surface of the flange facing toward the second cover.

A plurality of contact protrusions may be arranged to be spaced apart from each other in a circumferential direction with respect to the heater.

The contact protrusion may extend in a circumferential direction with respect to the heater.

The first cover and the second cover may be coupled to each other at outside of the contact protrusion.

The second cover may include an outer protrusion protruding from the outside of the contact protrusion toward the first cover and coupled to the first cover, and the first cover and the outer protrusion of the second cover extend in a circumferential direction with respect to the heater.

The flange may include a contact protrusion protruding toward the second cover and forming the other surface of the first cover supported by the second cover, and the second cover comprises a receiving groove receiving and supporting the other surface formed by the contact protrusion.

The second cover may include a mounting hole into which the other end of the heater is inserted; a receiving chamber extending outward from the heater and spaced apart from the outer surface of the heater to surround the heater; and a contact protrusion protruding from an inner surface of the receiving chamber toward the heater and contacting the other surface formed by the flange that faces toward the second cover.

A plurality of contact protrusions may be arranged to be spaced apart from each other along an outer surface of the flange.

The contact protrusion may extend along at least a part of an outer surface of the flange.

A wire for supplying electricity to the heater may be connected to the heater and the second cover may include a wire hole through which the wire passes.

The first cover may be integrally fixed to the outside of the heater by insert injection molding, the second cover may include a mounting hole into which the other end of the heater is inserted, and when the other end of the heater is inserted into the mounting hole, the second cover may be coupled to the first cover and supports the other surface of the first cover.

According to another aspect of the present disclosure, an aerosol generation device includes a heater assembly relating to the exemplary embodiments described above, a hollow case including a cigarette insertion hole open to outside and configured to receive the cigarette; and a battery disposed in the case to supply electricity to the heater assembly.

Advantageous Effects of Disclosure

In the heater assembly and the aerosol generation device including the same according to exemplary embodiments as described above, a second cover stably supports the other surface of a first cover that is coupled to a heater and maintains a position with respect to the heater and simultaneously the second cover supports the other end of the heater. As such, because a coupling interaction between the heater, the first cover, and the second cover is performed in a cooperative manner, a position of the heater disposed inside of the aerosol generation device may be firmly supported, and thus, relative movement (shaking and floating) of components of the heater assembly hardly occurs.

In addition, because the first cover and the second cover firmly support the heater, a state in which the heater assembly is mounted inside of the aerosol generation device is stably maintained, and thus, a defect due to repetitive use such as a poor coupling state of the heater assembly or disconnection of a wire for supplying electricity, etc. hardly occurs.

In addition, in the heater assembly in which the first cover and the heater are integrally formed by insert injection molding, the first cover and the heater are tightly coupled to each other, so no gap occurs in a coupling part of the first cover and the heater, which results in a perfect sealing effect.

Also, after the first cover and the heater are integrally formed by insert injection molding, because deformation of the first cover does not occur in post-processing for the heater assembly, in a process of coupling the heater assembly with other components, dimensions between the components precisely fit according to the initial design, and thus, a perfect product design may be implemented.

BEST MODE

With respect to the terms in the various exemplary embodiments of the present disclosure, the general terms which are currently and widely used are selected in consideration of functions of structural elements in the various exemplary embodiments of the present disclosure. However, meanings of the terms may be changed according to intention, a judicial precedent, appearance of a new technology, and the like. In addition, in certain cases, a term which is not commonly used may be selected. In such a case, the meaning of the term will be described in detail at the corresponding part in the description of the present disclosure. Therefore, the terms used in the various exemplary embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Hereinafter, exemplary embodiments of the present disclosure will be described in detail with reference to the accompanying drawings. The disclosure may, however, be embodied in many different forms and should not be construed as limited to the exemplary embodiments set forth herein.

Hereinafter, exemplary embodiments of the present disclosure will be described in detail with reference to the drawings.

Figure 1:
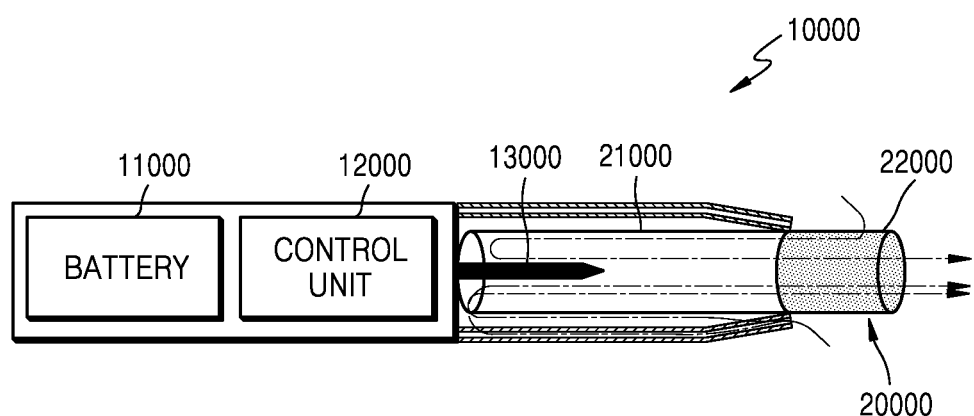
FIG. 1 is a diagram showing an example in which a cigarette is inserted into an aerosol generation device.

FIG. 1 is a diagram showing an example in which a cigarette is inserted into an aerosol generation device.

Referring to FIG. 1, the aerosol generation device 10000 includes a battery 11000, a control unit 12000, and a heater 13000. Also, the aerosol generation device 10000 is inserted into an inside space of the cigarette 20000.

FIG. 1 only shows certain elements of the aerosol generation device 10000 which are related to a particular exemplary embodiment. Therefore, it will be understood by one of ordinary skill in the art that the aerosol generation device 10000 may further include additional general purpose elements in addition to elements shown in FIG. 1.

Although FIG. 1 shows that the battery 11000, control unit 12000, and heater 13000 are arranged in line, the exemplary embodiments are not limited to this feature. In other words, arrangements of the battery 11000, control unit 12000, and heater can be changed according to design plan of the aerosol generating device 10000.

When the cigarette 20000 is inserted into the aerosol generating device 10000, the aerosol generating device 10000 heats the heater 13000. The temperature of an aerosol generating material in the cigarette 20000 is raised by the heated heater 13000, and thus aerosol is generated. The generated aerosol is delivered to a user through a cigarette filter 22000 of the cigarette 20000.

However, as necessary, even when a cigarette 20000 is not inserted into the aerosol generating device 10000, the aerosol generating device 10000 may heat the heater 13000.

The battery 11000 supplies power used for the aerosol generating device 10000 to operate. For example, the battery

11000 may supply power for heating the heater 13000 and supply power for operating the control unit 12000. In addition, the battery 11000 may supply power for operating a display, a sensor, a motor, and the like installed in the aerosol generating device 10000.

The control unit 12000 may control the overall operation of the aerosol generating device 10000. Specifically, the control unit 12000 may control not only operations of the battery 110 and the heater 13000, but also operations of other components included in the aerosol generating device 10000. The control unit 12000 may also check the status of each of the components of the aerosol generating device 10000 and determine whether the aerosol generating device 10000 is in an operable state.

The control unit 12000 may include at least one processor. A processor may be implemented by an array of a plurality of logic gates or may be implemented by a combination of a general purpose microprocessor and a memory in which a program executable in the microprocessor is stored. It will be understood by one of ordinary skill in the art that the present disclosure may be implemented in other forms of hardware.

The heater 13000 is heated by power supplied from the battery 11000. For example, when a cigarette is inserted into the aerosol generating device 10000, the heater 13000 can be located inside the cigarette. Therefore, the heated heater 13000 may raise the temperature of an aerosol generating material in the cigarette.

The heater 13000 may be an electrical resistive heater. For example, the heater 13000 may include an electrically conductive track, and the heater 13000 may be heated as electrical current flows through the electrically conductive track. But, the heater 13000 is not limited to the above example, and any heater structure being able to be heated to a desired temperature can be adapted. The desired temperature may be preset in the aerosol generating device 10000, or user may set up the desired temperature.

Meanwhile, as another example, the heater 13000 can be an inductive heater. To be specific, the heater 13000 may include electrical conductive coil for heating by an inductive heating method, and the cigarette may include a susceptor that can be heated by an inductive heater.

FIG. 1 shows that the heater 13000 is disposed to be inserted into the inside of the cigarette 20000, but the exemplary embodiments are not limited thereto. For example, the heater 13000 may include a pipe-shaped heating element, a plate-shaped heating element, a needle-shaped heating element, or a rod-shaped heating element. The heater 13000 may heat the inside or outside of the cigarette 20000 based on the shape of the heating element.

Also, the aerosol generating device 10000 may include a plurality of heaters 13000. Here, the plurality of heaters 13000 can be disposed to be inserted into inside of the cigarette 20000, or disposed outside of the cigarette 20000. Also, a part of the plurality of heaters 13000 may be disposed to be inserted into inside of the cigarette 20000, and the rest of the plurality of heaters 13000 may be disposed outside of the cigarette 20000. Also, the shape of the heater 13000 is not limited to the shape shown in FIG. 1, and may be manufactured into various shapes.

Meanwhile, the aerosol generating device 10000 may include additional general-purpose components other than the battery 11000, the control unit 12000, and the heater 13000. For example, the aerosol generating device 10000 may include a display capable of outputting visual information and/or a motor for outputting tactile information. The aerosol generating device 10000 may also include at least one sensor (e.g., a puff detecting sensor, a temperature sensing sensor, a cigarette insertion detecting sensor, etc).

Also, the aerosol generating device 10000 may be fabricated to have a structure in which the outside air may flow in/out even in the state where the cigarette 20000 is inserted.

Although now shown in FIG. 1, the aerosol generating device 10000 may form a part of the system along with an additional cradle. For example, the cradle may be used to charge the battery 11000 of the aerosol generating device 10000. Also, the heater 13000 may be heated while the cradle and the aerosol generating device 10000 are connected.

The cigarette 20000 may be similar to a general combustion-type cigarette. For example, the cigarette 20000 may include a first portion 21000 containing an aerosol generating material and a second portion 22000 including a filter and the like. Also, the cigarette 20000 may also include an aerosol generating material in the second portion 22000. For example, an aerosol generating material in the form of granules or capsules may be inserted into the second portion 22000.

The entire first portion 21000 may be inserted into the aerosol generating device 10000 and the second portion 22000 may be exposed to the outside. Alternatively, only a portion of the first portion 21000 may be inserted into the aerosol generating device 10000 or the entire first portion 21000 and a portion of the second portion 22000 may be inserted into the aerosol generating device 10000. A user may inhale the aerosol while holding the second portion 22000 by his/her lips. At this time, the aerosol is generated from the outside air passing through the first portion 21000, and generated aerosol is delivered to a user's mouth by passing through the second portion 22000.

As an example, the outside air can be introduced through at least one air passage formed in the aerosol generating device 10000. For example, opening and closing of the air passage formed in the aerosol generating device 10000 and/or a size of the air passage can be adjusted by user. Accordingly, the amount of smoke and a smoking impression may be adjusted by the user. As another example, the outside air may be introduced into inside of the cigarette 20000 through at least one hole formed in a surface of the cigarette 20000, Hereinafter, an exemplary embodiment of the cigarette 20000 will be explained referring to FIG. 2.

Figure 2:
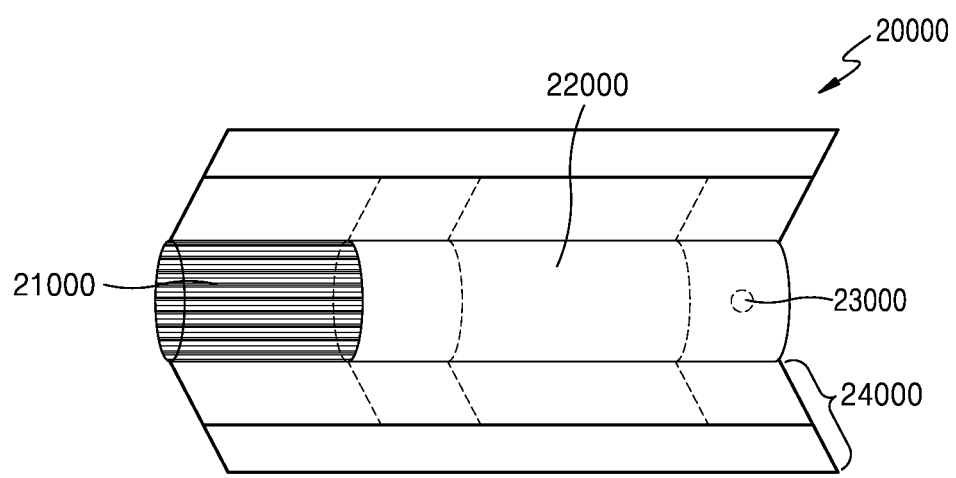
FIG. 2 is a diagram showing an example of a cigarette.

FIG. 2 is a diagram showing an example of a cigarette.

Referring to FIG. 2, the cigarette 20000 includes a tobacco rod 21000 and a filter rod 22000. The first portion 21000 described above referring to FIG. 1 may include the tobacco rod 210000, and the second portion 22000 may include the filter rod 22000.

Although the filter rod 22000 is shown as one segment in FIG. 2, the filter rod is not limited thereto. In other words, the filter rod 22000 can be formed as a plurality of segments. For example, the filter rod 22000 may include a first segment for cooling aerosol and a second segment for filtering some elements included in aerosol. Also, the filter rod 22000 may further include at least one segment performing different function as desired.

The cigarette 20000 may be packaged by at least one wrapper 24000. The wrapper 24000 may include at least one hole through which the outside air is introduced or inner gas is discharged. As an example, the cigarette 20000 may be packaged by one wrapper 24000. As another example, the cigarette 20000 may be packaged in an overlapped manner by at least two or more wrappers 24000. For example, the cigarette 21000 may be packaged by the first wrapper and the filter rod 22000 may be packaged by the second wrapper. Additionally, the tobacco rod 21000 and filter rod 22000 are connected after being packaged by separate wrappers, and then whole part of the cigarette 20000 can be packaged again by a third wrapper. If the tobacco rod 21000 or filter rod 22000 is made into a plurality of segments, each segment can be packaged by a separate wrapper. Also, whole part of the cigarette 2000 formed by connected segments, which are packaged by separate wrappers, can be packaged again by another wrapper.

The tobacco rod 21000 may include an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol, but not limited thereto. Also, the tobacco rod 21000 may include other additive materials like a flavoring agent, a wetting agent, and/or organic acid. Also, flavoring liquid like menthol or wetting material can be added into the tobacco rod 21000 by being sprayed onto the tobacco rod 21000.

The tobacco rod 21000 can be manufactured by various methods. For example, the tobacco rod 21000 can be formed by using a sheet, or a strand. Also, the tobacco rod 21000 can be formed by using tobacco leaves cut from tobacco sheet. Also, the tobacco rod 21000 can be surrounded by a thermal conductive material. For example, a thermal conductive material may include metal foil like aluminum foil, but not limited thereto. As one example, the thermal conductive material surrounding the tobacco rod 21000 may increase thermal conductivity by evenly dispersing heat which is conducted to tobacco rod 21000, and therefore increase taste of tobacco. Also, the thermal conductive material surrounding the tobacco rod 21000 may function as a susceptor being heated by an inductive heating type heater. In this case, although not shown in drawings, the tobacco rod 21000 may further include an additional susceptor in addition to the thermal conductive material surrounding the outside of tobacco rod 21000.

The filter rod 22000 may be a cellulose acetate filter. Meanwhile, the shape of the filter rod 22000 is not limited to a specific shape. For example, the filter rod 22000 can be a cylindrical shape type rod or a tube type rod with a hollow cavity therein. Also, the filter rod 22000 can be a recess type rod. If the filter rod 22000 is made of a plurality of segments, at least one of the plurality of segments may have a different shape than others.

The filter rod 22000 can be formed to generate flavor. For example, flavoring liquid can be sprayed on the filter rod 22000, or a separate fiber coated with flavoring liquid can be inserted into the inside of the filter rod 22000.

Also, the filter rod 22000 can include at least of one capsule 23000. Here, the capsule 23000 can generate a flavor or generate aerosol. For example, the capsule 23000 may have a configuration in which a content liquid containing a flavoring material is wrapped with a film. For example, the capsule 23000 may have a spherical or cylindrical shape.

If the filter rod 22000 includes a cooling segment for cooling aerosol, the cooling segment can be made from polymer or bio-degradable polymer. For example, the cooling segment may be formed by polylactic acid, but not limited thereto. Otherwise, the cooling segment may be made of a cellulose acetate filter having a plurality of holes. But, the cooling segment is not limited to the above described example, and any configuration capable of providing a cooling function can be used.

Figure 3:
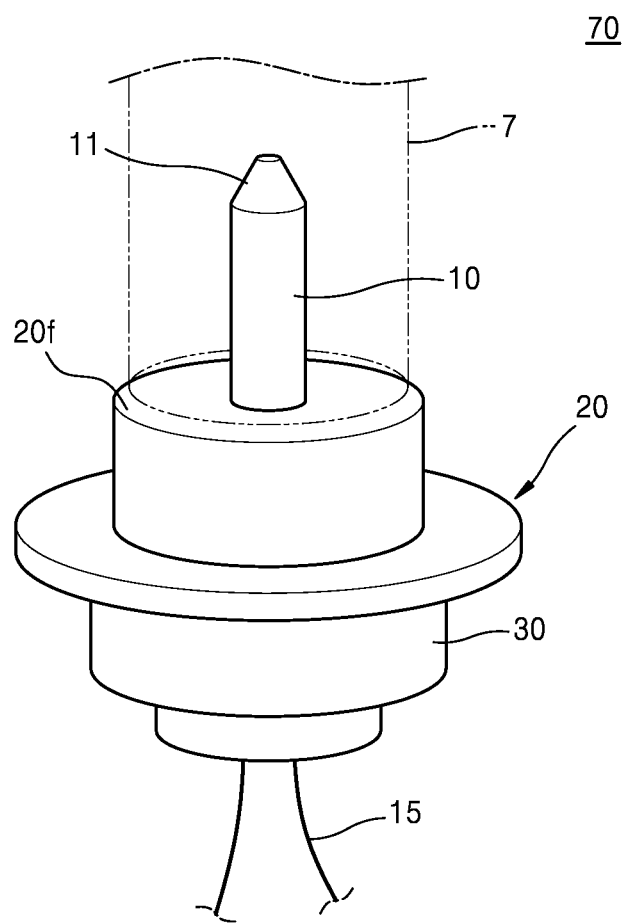
FIG. 3 is a perspective view of a heater assembly according to an embodiment.
Figure 4:
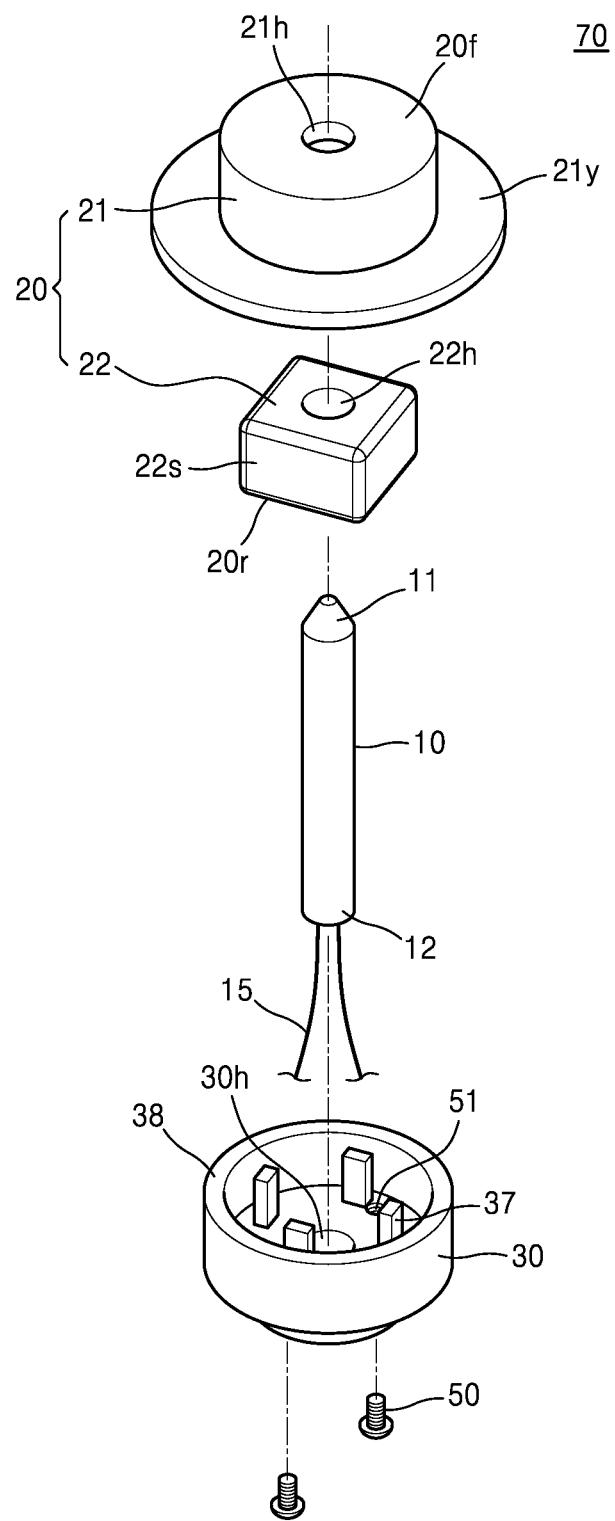
FIG. 4 is an exploded perspective view schematically illustrating a coupling relationship of components of the heater assembly according to the exemplary embodiment shown in FIG. 3.

FIG. 3 is a perspective view of a heater assembly 70 according to an exemplary embodiment, and FIG. 4 is an exploded perspective view schematically illustrating a coupling relationship of components of the heater assembly 70 according to the exemplary embodiment shown in FIG. 3.

The heater assembly 70 according to the exemplary embodiment shown in FIGS. 3 and 4 may be inserted into a cigarette 7. The heater assembly 70 may include a heater 10 that heats the cigarette 7 when electricity is applied from the outside, and a first cover 20 and a second cover 30 which support the heater 10.

The heater 10 may have a cylindrical shape or a rod shape extending in a longitudinal direction of the cigarette 7 to correspond to at least a part of the length of the cigarette 7. The heater 10 may have a diameter that is less than a diameter of the cigarette 7. A length of the heater 10 in an axial direction (where 'axial direction' means a longitudinal direction in which the central axis of the heater 10 extends) may be less than the length of the cigarette 7.

A shape of the heater 10 is not limited by the exemplary embodiments represented in the drawings, and the shape of the heater 10 may be variously modified. For example, the diameter of the heater 10 may be modified to be greater or less than that shown in FIG. 3 and may be manufactured in the shape of a needle.

One end 11 of the heater 10 may have a pointy shape, and thus, the one end 11 of the heater 10 may be easily inserted into the cigarette 7. In addition, a wire 15 for supplying electricity to the heater 10 is connected to the heater 10. The wire 15 may be electrically connected to an outer surface of the heater 10 by, for example, a welding process, such as soldering or ultrasonic welding.

The first cover 20 and the second cover 30 are coupled to the outside of the heater 10. The first cover 20 and the second cover 30 may be made of, for example, a heat resistant polymer material, a metal material, or a metal material or an alloy material coated with the heat resistant polymer material on a surface thereof.

The first cover 20 is coupled to the heater 10 to maintain a position with respect to the heater 10. One surface 20*f* facing toward the one end 11 of the heater 10 of the first cover 20 extends outward from the heater 10.

When the one end 11 of the heater 10 is inserted into the cigarette 7, the one surface 20*f* of the first cover 20 may be disposed facing toward an end portion of the cigarette 7 into which the one end 11 of the heater 10 is inserted and may support the end portion of the cigarette 7.

Figure 5:
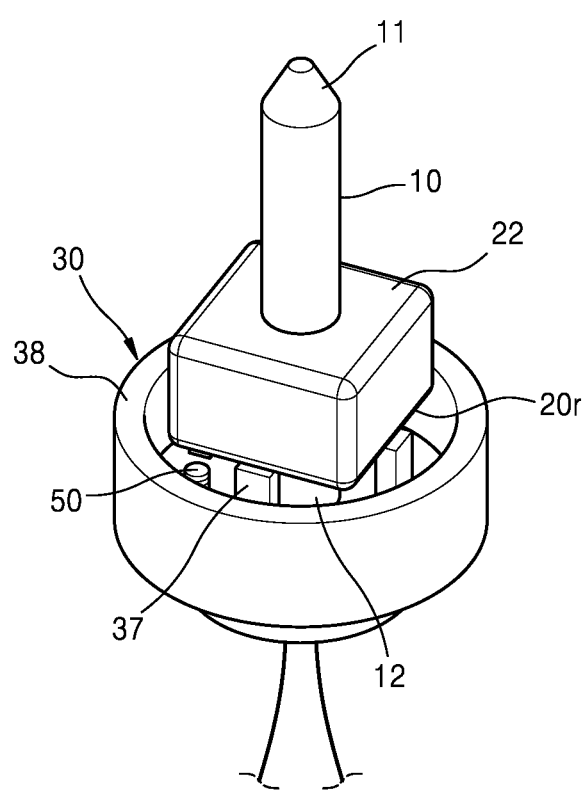
FIG. 5 is a perspective view showing some components inside of the heater assembly according to the exemplary embodiment shown in FIG. 3.
Figure 6:
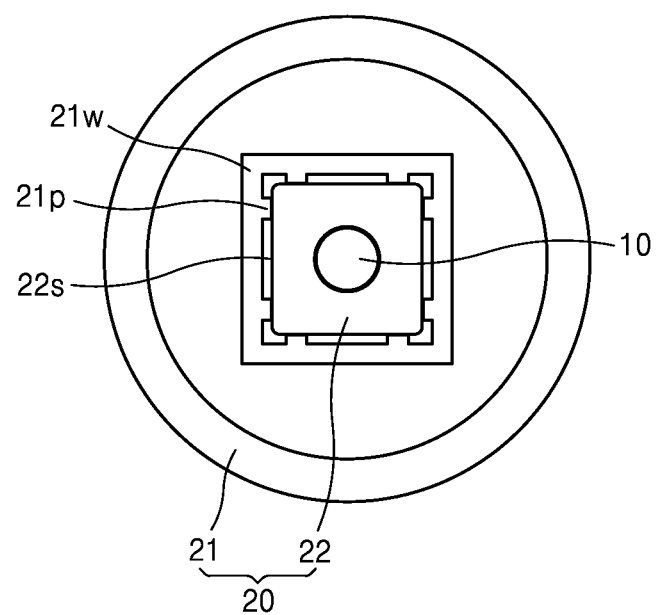
FIG. 6 is a cross-sectional view showing a transverse section of a part of the heater assembly according to the exemplary embodiment shown in FIG. 3.
Figure 7:
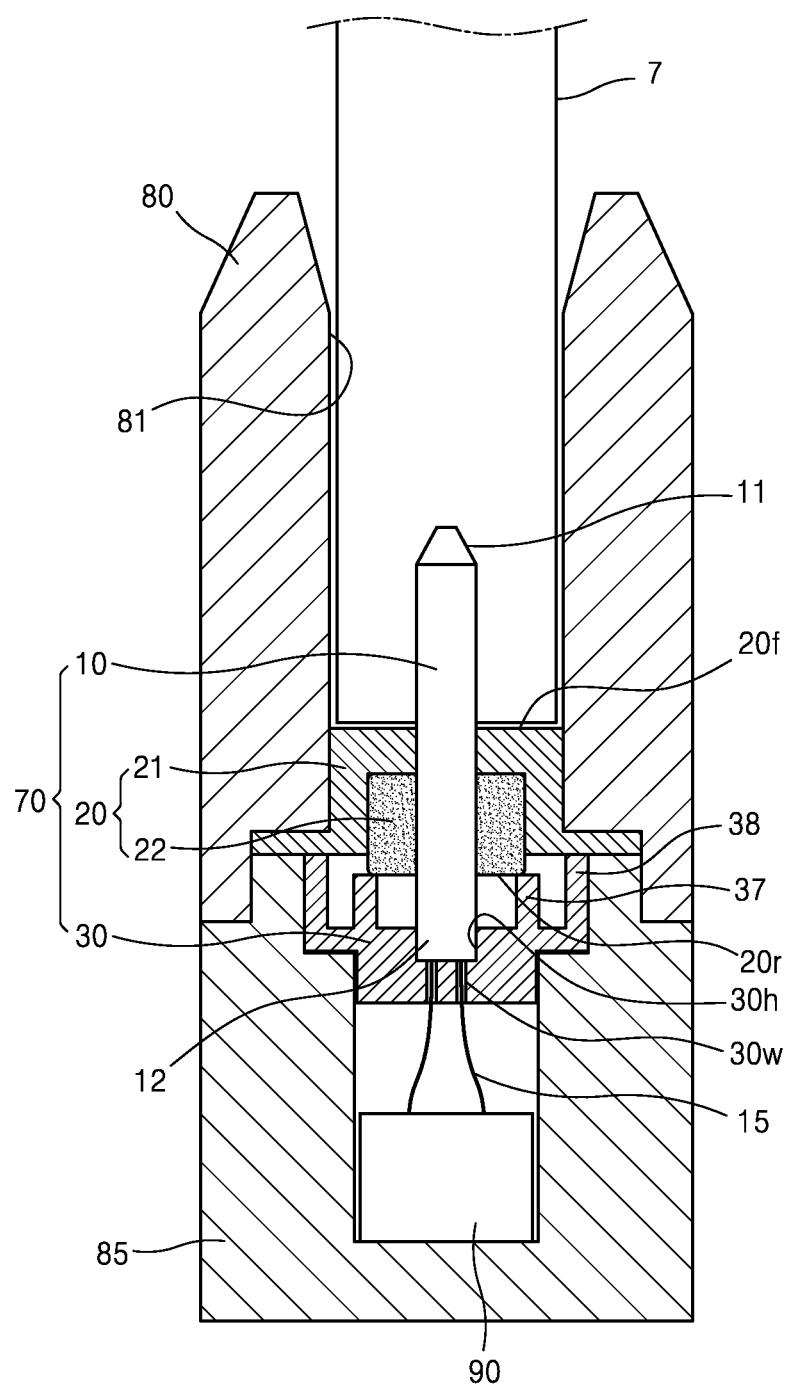
FIG. 7 is a cross-sectional view showing an aerosol generation device including the heater assembly according to the exemplary embodiment shown in FIG. 3.

FIG. 5 is a perspective view showing some components inside of the heater assembly 70 according to the exemplary embodiment shown in FIG. 3. FIG. 6 is a cross-sectional view showing a transverse section of a part of the heater assembly 70 according to the exemplary embodiment shown in FIG. 3. FIG. 7 is a cross-sectional view showing an aerosol generation device including the heater assembly 70 according to the exemplary embodiment shown in FIG. 3.

Referring to FIGS. 5 and 7, the second cover 30 is coupled to the other end 12 of the heater 10. The second cover 30 may support the other end 12 of the heater 10 and may also support the first cover 20.

In assembling the heater assembly 70, the first cover 20 is first coupled to the heater 10 such that the first cover 20 maintains a position with respect to the heater 10. When the first cover 20 is first coupled to the heater 10 and then the second cover 30 is coupled to the heater 10, the second cover 30 is coupled to the other end 12 of the heater 10 and simultaneously, the second cover 30 is also coupled to the first cover 20. As such, the second cover 30 also stably maintains a position with respect to the heater 10.

When the second cover 30 is coupled to the other end 12 of the heater 10, the second cover 30 may support the other surface 20r of the first cover 20 facing toward the other end 12 of the heater 10.

The first cover 20 includes a flange 22 fixed to an outer surface of the heater 10 and protruding outward from the outer surface of the heater 10, and also includes an outer cover 21 disposed closer to the one end 11 of the heater 10 than the flange 22. The outer cover 21 may form the one surface 20f of the first cover 20, contacting and supporting at least a part of an outer surface 22s of the flange 22. The other surface 20r of the first cover 20 supported by the second cover 30 may be formed by a lower surface of the flange 22.

The outer cover 21 of the first cover 20 includes a coupling hole 21h through which the one end 11 of the heater 10 passes. In addition, the first cover 20 includes a mounting plate 21y extending in a circumferential direction with respect to the heater 10, that is, with respect to the coupling hole 21h, so as to function as a support structure for coupling with the second cover 30.

The flange 22 includes a through hole 22h through which the one end 11 of the heater 10 passes. The through hole 22h is directly coupled to an outer surface of the heater 10. The flange 22 may be made of a material having heat resistance and durability, such as alumina, ceramic, Teflon, and heat resistant plastic.

When combining the flange 22 and the heater 10, the heater 10 may be first inserted into the through hole 22h of the flange 22 to set the position of the flange 22 with respect to the heater 10, and then ceramic bond may be injected into the through hole 22h of the flange 22 to temporarily fix the flange 22 and the heater 10. Thereafter, an assembly of the flange 22 and the heater 10 may be placed in a sintering furnace to apply heat such that the flange 22 and the heater 10 may be completely fixed.

The exemplary embodiment is not limited by the coupling method of the flange 22 and the heater 10 described above, and the flange 22 and the heater 10 may be coupled using various methods. For example, a screw coupling structure may be applied between the flange 22 and the heater 10, or a one-touch fastening structure such as a bayonet mount may be applied between the flange 22 and the heater 10. The flange 22 and the heater 10 may be joined using an adhesive, or the flange 22 may be provided to the outside of the heater 10 by applying an insert injection process according to a material of the flange 22.

Referring to FIG. 6, the first cover 20 includes an inner wall surface 21w extending along the outer surface 22s of the flange 22 to surround the outer surface 22s of the flange 22 coupled to the heater 10. The inner wall surface 21w is provided spaced apart by a predetermined gap from the outer surface 22s of the flange 22.

The first cover 20 includes an inner protrusion 21p that protrudes from the inner wall surface 21w and contacts the outer surface 22s of the flange 22 to support the outer surface 22s. A plurality of inner protrusions 21p of the first cover 20 may be disposed to be spaced apart along the outer surface 22s of the flange 22.

In the exemplary embodiment shown in the drawing, cross-sectional shapes of the flange 22 and the inner wall surface 21w in a transverse direction are substantially square shapes, but the exemplary embodiment is not limited by the shapes of the flange 22 and the inner wall surface 21w. For example, the flange 22 may have a circular, elliptical, or polygonal cross-sectional shape, and the cross-sectional shape of the inner wall surface 21w of the first cover 20 may also be modified to correspond to the cross-sectional shape of the flange 22.

The second cover 30 also extends in a circumferential direction in accordance with the first cover 20. The second cover 30 includes a mounting hole 30h into which the other end 12 of the heater 10 is inserted, and also includes a contact protrusion 37 protruding from the outside of the mounting hole 30h in a direction toward the flange 22 (i.e., in a direction toward the one end 11 of the heater 10). The contact protrusion 37 may directly contact the other surface 20r of the flange 22 toward the second cover 30 to stably support the flange 22 of the first cover 20.

A plurality of contact protrusions 37 of the second cover 30 may be arranged to be spaced apart in the circumferential direction with respect to the mounting hole 30h. The number, installation positions or shapes of the contact protrusions 37 are not limited by the configuration of the exemplary embodiment shown in FIG. 4, and the number and installation positions and shapes of the contact protrusions 37 may be variously modified.

The first cover 20 and the second cover 30 may be coupled to each other on the outside of the contact protrusion 37. The second cover 30 includes an outer protrusion 38 that protrudes from the outside of the contact protrusion 37 toward the first cover 20. The mounting plate 21y of the first cover 20 extends in the circumferential direction with respect to the heater 10, and the outer protrusion 38 of the second cover 30 may also extend in the circumferential direction in accordance with the shape of the first cover 20.

Referring to FIGS. 4 and 5, the first cover 20 and the second cover 30 may be coupled to each other by a bolt 50, which is an example of fastening means. The bolt 50 passes through a bolt through hole 51 formed in the second cover 30 and then is screwed into a screw hole (not shown) formed in the first cover 20 such that a coupling state of the first cover 20 and the second cover 30 may be stably maintained.

A method of coupling the first cover 20 and the second cover 30 to each other is not limited only to a fastening method by the bolt 50 described in the embodiment. For example, a different form of fastening means such as a rivet or a pin may be used. Also, a bonding method using an adhesive may be used. Also, a welding method using ultrasonic waves or heat may be used. Also, a configuration such as protrusions, hooks, clips, coupling grooves, etc. may be applied to both sides of the first cover 20 and the second cover 30. Also, screw surfaces corresponding to each other may be provided on both sides of the first cover 20 and the second cover 30. Also, a one-touch fastening structure such as a bayonet mount may be applied, and thus, the configuration that the first cover 20 and the second cover 30 are coupled to each other may be implemented.

Alternatively, the outer protrusion 38 and the mounting plate 21y may be coupled to each other and thus the first cover 20 and the second cover 30 may be fixed to each other.

In the heater assembly 70 having the above-described configuration, when the first cover 20 and the second cover 30 are coupled to the heater 10, the second cover 30 stably supports the other surface 20r of the first cover 20 while the first cover 20 supports the heater 10 and the second cover 30 also supports the heater 10. Thus, a coupling interaction between the heater 10, the first cover 20, and the second cover 30 is performed in a cooperative manner. Therefore, in a state where the heater 10, the first cover 20, and the second cover 30 are coupled to each other, relative movement (shaking and floating) of the heater 10 with respect to the first cover 20 and the second cover 30 does not occur.

Referring to FIG. 7, the aerosol generation device according to the exemplary embodiment shown in FIG. 7 includes a case 80 capable of accommodating the cigarette 7 and the heater assembly 70 disposed in the case 80 to heat the cigarette 7.

The case 80 constitutes an outer appearance of the aerosol generation device, and accommodates and protects various components in a space formed therein. The case 80 includes a cigarette insertion hole having a hollow cylindrical shape and open to the outside at a front end thereof such that the cigarette 7 may be inserted.

The case 80 may be made of a plastic material that does not conduct electricity and heat, or a metallic material coated with a plastic material on a surface thereof. In the exemplary embodiment, the case 80 has the cylindrical shape having a circular cross-section, but the exemplary embodiment is not limited by a configuration of the case 80. For example, the case 80 may have a cylindrical shape having a polygonal cross-section such as a quadrangle.

The case 80 has a passage 81 for accommodating the cigarette 7. The heater assembly 70 that heats the cigarette 7 is coupled to the case 80. The one end 11 of the heater 10 of the heater assembly 70 is disposed inside of the passage 81 of the case 80, and when the cigarette 7 is accommodated in the case 80, the one end 11 of the heater 10 is inserted into a bottom surface of an end portion of the cigarette 7.

The other end 12 of the heater 10 is electrically connected to a battery 90 disposed at the rear of the case 80 through the wire 15. The second cover 30 includes a wire hole 30w through which the wire 15 passes. One end of the wire 15 is electrically connected to the heater 10, and the other end of the wire 15 is electrically connected to the battery 90 through the wire hole 30w of the second cover 30.

A base 85 surrounding the battery 90 is connected to the rear of the case 80. When electricity of the battery 90 is supplied to the heater 10 in a state where the cigarette 7 is inserted into the one end 11 of the heater 10, the heater 10 is heated and thus the cigarette 7 is heated.

When a user of the aerosol generation device mounts the cigarette 7 to the case 80, the cigarette 7 is inserted into the passage 81 of the case 80 and moves along the passage 81. When the end portion of the cigarette reaches the one surface 20f of the first cover 20 of the heater assembly 70, a user's hand holding the cigarette 7 may sense the end portion of the cigarette 7 touching the one surface 20f of the first cover 20. Therefore, by simply pushing the cigarette 7 into the passage 81, the user may easily mount the cigarette 7 to the aerosol generation device.

In the heater assembly 70 having the above-described configuration, the first cover 20 and the second cover 30 firmly maintain their positions with respect to the heater 10 such that the first cover 20 and the second cover 30 do not move with respect to the heater 10 in a state of being coupled to the outside of the heater 10.

When the heater assembly 70 is mounted to the case 80 of the aerosol generation device, the first cover 20 and the second cover 30 are fixed to the inside of the case 80, and thus, a position and a mounting state of the heater assembly 70 mounted inside of the case 80 may be stably maintained.

As the aerosol generation device is repeatedly used, an operation of inserting the one end 11 of the heater 10 into the cigarette 7 when the cigarette 7 is mounted to the case 80 and an operation of removing the cigarette 7 from the one end 11 of the heater 10 when the cigarette 7 is separated from the case 80 are repeated.

In the heater assembly 70 having the above-described configuration, the first cover 20 and the second cover 30 firmly support the heater 10, and thus, a state where the heater assembly 70 is mounted inside of the case 80 of the aerosol generation device is stably maintained. Therefore, defects due to repetitive use such as a poor coupling state of the heater assembly 70 or a disconnection of the wire 15 for supplying electricity to the heater 10 is disconnected, etc. may be prevented.

MODE OF DISCLOSURE

Figure 8:
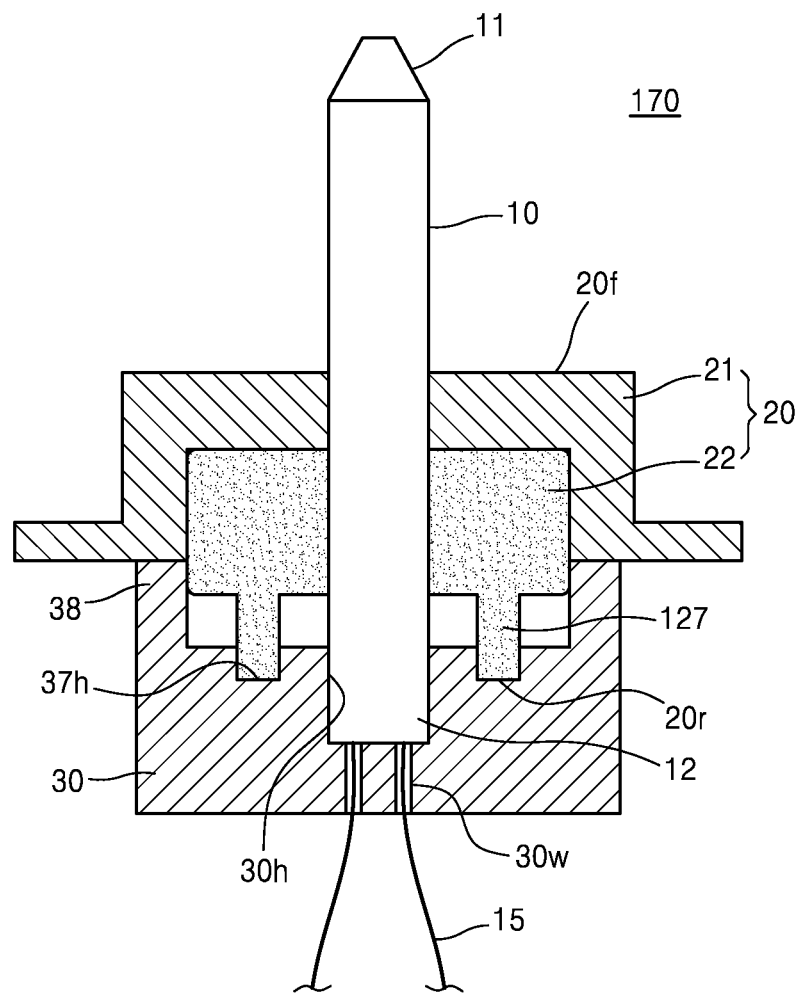
FIG. 8 is a longitudinal cross-sectional view of a heater assembly according to another embodiment.

FIG. 8 is a longitudinal cross-sectional view of a heater assembly 170 according to an exemplary embodiment.

The heater assembly 170 according to the exemplary embodiment shown in FIG. 8 may include the heater 10 to be inserted into a cigarette to generate heat when electricity is applied from the outside to heat the cigarette. The heater assembly 170 may include the first cover 20 that is coupled to the heater 10 to maintain a position with respect to the heater 10. The first cover 20 may have the one surface 20f near the one end 11 of the heater 10, which extends outward from the heater 10. The heater assembly 170 may include the second cover 30 that is coupled to the other end 12 of the heater 10 and supports the other surface 20r of the first cover 20 facing toward the other end 12 of the heater 10.

The first cover 20 includes a flange 22 fixed to an outer surface of the heater 10 and protruding outward from the outer surface of the heater 10 and an outer cover 21 disposed at a position closer to the one end 11 of the heater 10 than a position of the flange 22 to form the one surface 20f of the first cover 20 and contacting and supporting an outer surface of the flange 22.

In the heater assembly 170 according to the exemplary embodiment shown in FIG. 8, the flange 22 includes a contact protrusion 127 protruding toward the second cover 30. The contact protrusion 127 forms at least a part of the other surface 20r from the first cover 20 toward the other end 12 of the heater 10. The second cover 30 may include a receiving groove 37h receiving the other surface 20r of the contact protrusion 127 to support the other surface 20r of the contact protrusion 127.

A plurality of contact protrusions 127 may be disposed to be spaced apart from each other in a circumferential direction with respect to the heater 10. A plurality of receiving grooves 37h of the second cover 30 that receive the other surface 20r of the contact protrusion 127 may be also disposed to be spaced apart from each other in the circumferential direction with respect to the heater 10 in correspondence to the number of contact protrusions 127.

The exemplary embodiment is not limited by configurations of the contact protrusion 127 of the flange 22 and the receiving groove 37h of the second cover 30, and the contact protrusion 127 and the receiving groove 37h may be variously modified. For example, the contact protrusion 127 may extend in some sections of the circumferential direction with respect to the heater 10 to have a circular ring shape extending in the circumferential direction with respect to the heater 10 or an arc shape with respect to the heater 10. In correspondence thereto, the receiving groove 37h of the second cover 30 may also have the circular ring shape or the arc shape.

In the heater assembly 170 having the above-described configuration, when the first cover 20 and the second cover 30 are coupled to the heater 10, the second cover 30 stably supports the other surface 20r formed by the contact protrusion 127 protruding toward the second cover 30 in the flange 22 of the first cover 20 while the first cover 20 supports the heater 10 and the second cover 30 also supports the heater 10. Thus, coupling interactions between the heater 10, the first cover 20, and the second cover 30 may be performed in a cooperative manner. Therefore, in a state where the heater 10, the first cover 20, and the second cover 30 are coupled to each other, relative movement (shaking and floating) of the heater 10 with respect to the first cover 20 and the second cover 30 does not occur.

Figure 9:
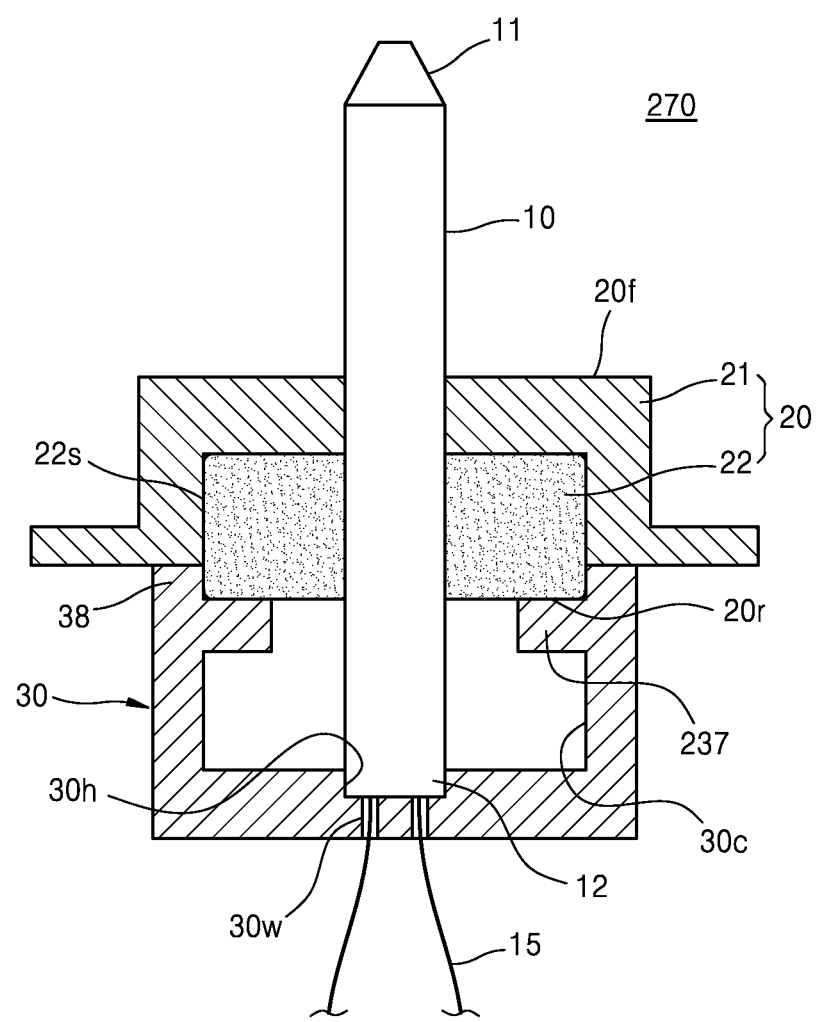
FIG. 9 is a longitudinal cross-sectional view of a heater assembly according to another embodiment.

FIG. 9 is a longitudinal cross-sectional view of a heater assembly 270 according to an exemplary embodiment.

The heater assembly 270 according to the exemplary embodiment shown in FIG. 9 may include the heater 10 that may be inserted into a cigarette and may generate heat when electricity is applied from the outside to heat the cigarette. The heater assembly 270 may include the first cover 20 coupled to the heater 10 and maintains a position with respect to the heater 10. The first cover 20 may have the one surface 20f facing toward the one end 11 of the heater 10 and extending outward from the heater 10. The heater assembly 270 may include the second cover 30 coupled to the other end 12 of the heater 10 and support the other surface 20r of the first cover 20 facing toward the other end 12 of the heater 10.

The first cover 20 includes a flange 22 fixed to an outer surface of the heater 10 and protruding outward from the outer surface of the heater 10. The first cover 20 includes an outer cover 21 which is disposed closer to the one end 11 of the heater 10 than the flange 22 to form the one surface 20f of the first cover 20, and contacts and supports the outer surface 22s of the flange 22. The other surface 20r of the first cover 20 supported by the second cover 30 is formed by a lower surface of the flange 22.

When the second cover 30 is coupled to the other end 12 of the heater 10, the second cover 30 may support the other surface 20r of the first cover 20 facing toward the other end 12 of the heater 10.

In the heater assembly 270 according to the exemplary embodiment shown in FIG. 9, an installation position of a contact protrusion 237 of the second cover 30 for supporting the other surface 20r of the first cover 20 is modified.

The second cover 30 includes the mounting hole 30h into which the other end 12 of the heater 10 is inserted, a receiving chamber 30c extending outward from the heater 10 so as to be spaced outward from the outer surface of the heater 10 and surrounding the heater 10, and a contact protrusion 237 protruding from an inner surface of the receiving chamber 30c toward the outer surface of the heater 10 and contacting the other surface 20r of the flange 22.

A plurality of contact protrusions 237 may be installed to be spaced apart along the outer surface 22s of the flange 22. However, the exemplary embodiment is not limited by a structure of the contact protrusion 237, and thus, the structure of the contact protrusion 237 may be variously modified.

For example, the contact protrusion 237 may be formed to extend along the other surface 20r of the flange 22. In other words, when the flange 22 has a circular or elliptical transverse cross-section, the contact protrusion 237 may have a circular or elliptical shape extending in a circumferential direction along an extension direction of the outer surface 22s of the flange 22, or an arc shape extending in some sections of the circumferential direction of the extension direction of the outer surface 22s of the flange 22. In addition, when the flange 22 has a polygonal transverse cross-section, the contact protrusion 237 may also have a polygonal shape extending along the other surface 20r of the flange 22.

In the heater assembly 170 having the above-described configuration, when the first cover 20 and the second cover 30 are coupled to the heater 10, the contact protrusion 237 protruding toward the heater 10 from the inner surface of the receiving chamber 30c of the second cover 30 stably supports the other surface 20r of the first cover 20 formed on the flange 22 while the first cover 20 supports the heater 10 and the second cover 30 also supports the heater 10. Thus, a coupling interaction between the heater 10, the first cover 20, and the second cover 30 is performed in a cooperative manner. Therefore, in a state where the heater 10, the first cover 20, and the second cover 30 are coupled to each other, relative movement (shake and floating) of the heater 10 with respect to the first cover 20 and the second cover 30 does not occur.

Figure 10:
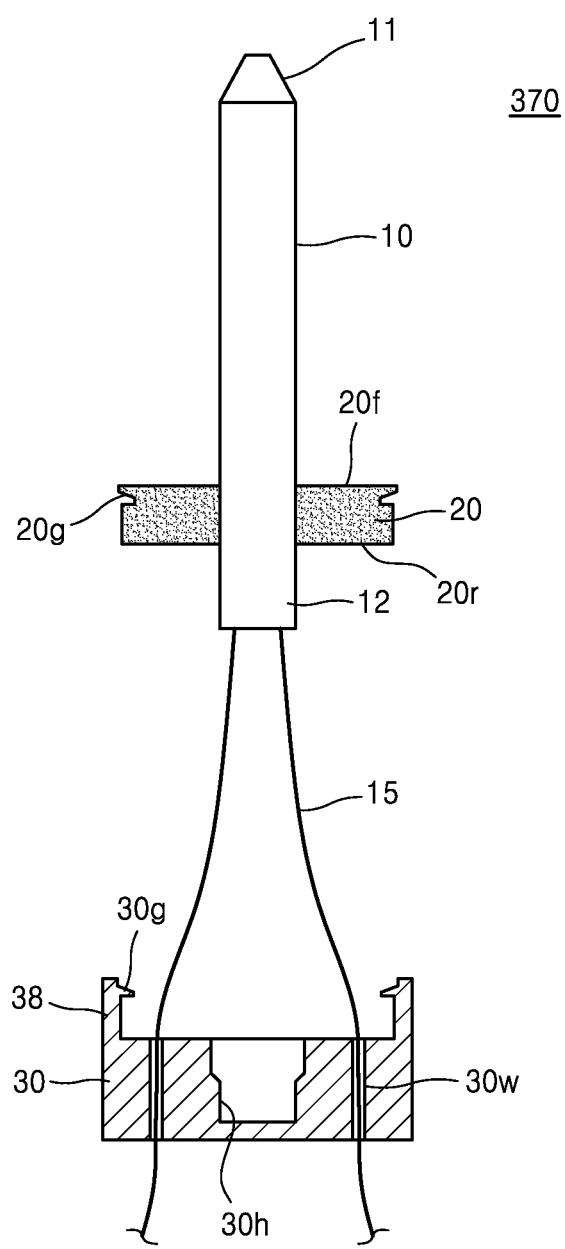
FIG. 10 is an exploded perspective view schematically illustrating a coupling relationship of components of a heater assembly according to another embodiment.
Figure 11:
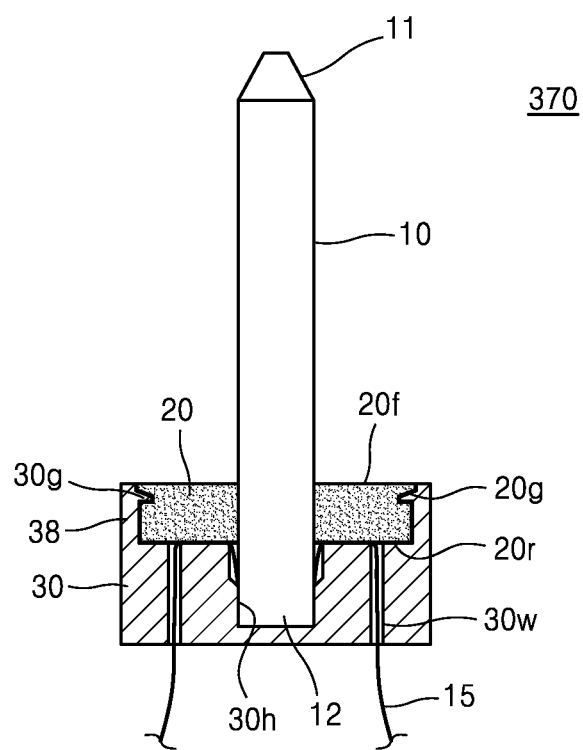
FIG. 11 is a cross-sectional view of the heater assembly according to the exemplary embodiment shown in FIG. 10.

FIG. 10 is an exploded perspective view schematically illustrating a coupling relationship of components of a heater assembly 370 according to another embodiment. FIG. 11 is a cross-sectional view of the heater assembly 370 according to the exemplary embodiment shown in FIG. 10.

The heater assembly 370 according to the exemplary embodiment shown in FIGS. 10 and 11 may include the heater 10 that may be inserted into a cigarette and generate heat when electricity is applied from the outside to heat the cigarette. The heater assembly 370 may include the first cover 20 that may be coupled to the heater 10 and maintain a position with respect to the heater 10. The first cover 20 may have the one surface 20f facing toward the one end 11 of the heater 10 extending outward from the heater 10. The heater assembly 370 may include the second cover 30 that may be coupled to the other end 12 of the heater 10 and support the other surface 20r of the first cover 20 facing toward the other end 12 of the heater 10.

In the heater assembly 370 according to the exemplary embodiment shown in FIGS. 10 and 11, a configuration of the first cover 20 is modified. The first cover 20 is integrally fixed to the outside of the heater 10 by insert injection molding. That is, after the heater 10 is first made of a metal or alloy material, the heater 10 is placed in a previously prepared mold, and then a molten heat resistant plastic (resin) solution is injected into the mold and then cooled, and thus, the first cover 20 is installed in the outside of the heater 10. According to such an insert injection molding, the heater 10 and the first cover 20 may be integrated into one body and completely fixed to each other.

FIG. 10 illustrates an example of an operation of assembling the second cover 30 with an assembly of the heater 10 and the first cover 20 after the heater 10 and the first cover 20 are integrated by insert injection molding.

The second cover 30 includes the mounting hole 30h into which the other end 12 of the heater 10 is inserted. When the other end 12 of the heater 10 is inserted into the mounting hole 30h of the second cover 30, the second cover 30 is coupled to the first cover 20, and thus, the second cover 30 may firmly support the other surface 20r of the first cover 20.

In order to firmly couple the first cover 20 and the second cover 30 to each other, a fastening structure using a hook and a coupling groove is applied between the first cover 20 and the second cover 30.

Referring to FIGS. 10 and 11, the first cover 20 includes a coupling groove 20g in an outer surface thereof in a radial direction. The second cover 30 includes an outer protrusion 38 protruding from an outer side of the mounting hole 30h toward the first cover 20, and the outer protrusion 38 includes a hook 30g protruding inward so as to be inserted into the coupling groove 20g of the first cover 20.

The second cover 30 includes a wire hole 30w through which the wire 15 passes. When the other end 12 of the heater 10 is inserted into the mounting hole 30h of the second cover 30 in a state where the wire 15 is inserted into the wire hole 30w, a coupling operation of the second cover 30 and the first cover 20 is performed together. That is, as the second cover 30 moves toward the first cover 20, the hook 30g of the outer protrusion 38 of the second cover 30 is slightly open and then inserted into the coupling groove 20g of the first cover 20, and thus, the hook 30g and the coupling groove 20g are completely coupled.

As such, the hook 30g and the coupling groove 20g are coupled to each other and stably maintain the coupling a state. In a state where the second cover 30 is coupled to the first cover 20, the second cover 30 may firmly support the other surface 20r of the first cover 20 facing toward the other end 12 of the heater 10.

In the heater assembly 370 having the above-described configuration, the first cover 20 and the heater 10 are completely fixed to each other to form an integral body by insert injection molding. When the second cover 30 is coupled to an assembly of the first cover 20 and the heater 10, which are integrally formed by insert injection molding, the second cover 30 may firmly support the other surface 20r of the first cover 20 and simultaneously support the other end 12 of the heater 10.

As such, a coupling interaction between the heater 10, the first cover 20, and the second cover 30 is performed in a cooperative manner, and thus, in a state where the heater 10, the first cover 20, and the second cover 30 are coupled to each other, relative movement (shaking and floating) of the heater 10 with respect to the first cover 20 and the second cover 30 may be prevented.

In addition, in the heater assembly 370 having the above-described configuration, the tight coupling of the first cover 20 and the heater 10 by insert injection molding leaves no gap between the first cover 20 and the heater 10, and thus, a good sealing effect may be obtained. That is, because it is difficult for a material generated during a process of generating aerosol by heating a cigarette using the heater 10 inserted into the cigarette or impurities introduced into an aerosol generation device from the outside to be introduced through a coupling part between the heater 10 and the first cover 20, the sealing effect of preventing an external material from being introduced toward the other end 12 of the heater 10 is improved.

In addition, when a method of integrally forming the first cover 20 and the heater 10 by insert injection molding is used, a dimension precision between components is improved as compared to a method of heating the heater 10 and the first cover 20 in a sintering furnace. That is, after the first cover 20 and the heater 10 are integrally formed by insert injection molding, deformation of the first cover 20 does not occur in post-processing for manufacturing the heater assembly 370 and a shape of the first cover 20 is maintained. Therefore, in a process of assembling the first cover 20 and the second cover 30 or in a process of coupling the heater assembly 370 with the aerosol generation device or with other components, dimensions between the components precisely fit according to the initial design, and thus, a perfect product design may be implemented.

Also, in the heater assembly 370 having the above-described configuration, the first cover 20 and the second cover 30 firmly support the heater 10, and a state where the heater assembly 370 is mounted inside of the aerosol generation device is stably maintained. Therefore, even when an operation of inserting the heater 10 into a cigarette and separating the cigarette from the heater 10 is repeatedly performed, because a coupling state of the components of the heater assembly 370 is maintained to be firm, a phenomenon of shaking between the components hardly occurs, and thus, defects such as disconnection of the wire 15 for supplying electricity to the heater 10 hardly occur.

It will be understood by one of ordinary skill in the art that various changes in form and details may be made therein without departing from the spirit and scope of the invention as defined by the appended claims. Therefore, the disclosed methods should be considered from an illustrative point of view, not from a restrictive point of view. The scope of the present disclosure is defined by the appended claims rather than by the foregoing description, and all differences within the scope of equivalents thereof should be construed as being included in the present disclosure.

INDUSTRIAL APPLICABILITY

Provided are a heater assembly with enhanced durability obtained by firmly maintaining an assembling state and an aerosol generation device including the same.

The invention claimed is:
1. A heater assembly comprising:
   a heater extending to correspond to at least a part of a length of a cigarette and comprising one end to be inserted into the cigarette and configured to generate heat when electricity is applied;
   a first cover coupled to the heater to maintain a position with respect to the heater and comprising one surface that faces toward the end of the heater and extends outward from the heater; and
   a second cover coupled to another end of the heater and supporting another surface of the first cover facing toward the other end of the heater,
   wherein the first cover comprises:
   a flange fixed to an outer surface of the heater and protruding outward from the outer surface of the heater; and
   an outer cover disposed closer to the one end of the heater than the flange to form the one surface of the first cover, and configured to contact and support at least a part of an outer surface of the flange, and
   wherein the other surface of the first cover supported by the second cover is formed by the flange.
2. The heater assembly of claim 1, wherein
   the outer cover further comprises an inner protrusion protruding from an inner side of the outer cover and contacting the outer surface of the flange.
3. The heater assembly of claim 1, wherein the second cover comprises:
   a mounting hole into which the other end of the heater is inserted; and
   a contact protrusion protruding from outside of the mounting hole toward the flange to contact the other surface of the flange facing toward the second cover.
4. The heater assembly of claim 3, wherein
   a plurality of contact protrusions are arranged to be spaced apart from each other in a circumferential direction with respect to the heater.
5. The heater assembly of claim 3, wherein
   the contact protrusion extends in a circumferential direction with respect to the heater.
6. The heater assembly of claim 3, wherein
   the first cover and the second cover are coupled to each other at outside of the contact protrusion.

7. The heater assembly of claim 6, wherein
the second cover comprises an outer protrusion protruding from the outside of the contact protrusion toward the first cover and coupled to the first cover, and
the first cover and the outer protrusion of the second cover extend in a circumferential direction with respect to the heater.

8. The heater assembly of claim 1, wherein
the flange comprises a contact protrusion protruding toward the second cover and forming the other surface of the first cover supported by the second cover, and
the second cover comprises a receiving groove receiving and supporting the other surface formed by the contact protrusion.

9. The heater assembly of claim 1, wherein the second cover comprises:
a mounting hole into which the other end of the heater is inserted;
a receiving chamber extending outward from the heater and spaced apart from the outer surface of the heater to surround the heater; and
a contact protrusion protruding from an inner surface of the receiving chamber toward the heater and contacting the other surface formed by the flange that faces toward the second cover.

10. The heater assembly of claim 9, wherein
a plurality of contact protrusions are arranged to be spaced apart from each other along an outer surface of the flange.

11. The heater assembly of claim 9, wherein
the contact protrusion extends along at least a part of an outer surface of the flange.

12. The heater assembly of claim 1, wherein
a wire for supplying electricity to the heater is connected to the heater and the second cover comprises a wire hole through which the wire passes.

13. The heater assembly of claim 1, wherein
the first cover is integrally fixed to outside of the heater by insert injection molding,
the second cover comprises a mounting hole into which the other end of the heater is inserted, and
when the other end of the heater is inserted into the mounting hole, the second cover is coupled to the first cover and supports the other surface of the first cover.

14. An aerosol generation device comprising:
a hollow case comprising:
a cigarette insertion hole open to outside and configured to receive a cigarette; and
a heater assembly comprising:
a heater extending to correspond to at least a part of a length of the cigarette and comprising one end to be inserted into the cigarette and configured to generate heat when electricity is applied;
a first cover coupled to the heater to maintain a position with respect to the heater and comprising one surface that faces toward the end of the heater and extends outward from the heater; and
a second cover coupled to another end of the heater and supporting another surface of the first cover facing toward the other end of the heater; and
a battery disposed in the hollow case and configured to supply electricity to the heater assembly,
wherein the first cover comprises:
a flange fixed to an outer surface of the heater and protruding outward from the outer surface of the heater; and
an outer cover disposed closer to the one end of the heater than the flange to form the one surface of the first cover, and configured to contact and support at least a part of an outer surface of the flange, and
wherein the other surface of the first cover supported by the second cover is formed by the flange.

15. The aerosol generation device of claim 8, wherein
the outer cover further comprises an inner protrusion protruding from an inner side of the outer cover and contacting the outer surface of the flange.

16. The aerosol generation device of claim 8, wherein
a mounting hole into which the other end of the heater is inserted; and
a contact protrusion protruding from outside of the mounting hole toward the flange to contact the other surface of the flange facing toward the second cover.

17. The aerosol generation device of claim 16, wherein
a plurality of contact protrusions are arranged to be spaced apart from each other in a circumferential direction with respect to the heater.

18. The aerosol generation device of claim 16, wherein
the contact protrusion extends in a circumferential direction with respect to the heater.

* * * * *